(12) United States Patent
Hunter et al.

(10) Patent No.: US 10,646,373 B2
(45) Date of Patent: *May 12, 2020

(54) EJECTOR MECHANISM, EJECTOR DEVICE, AND METHODS OF USE

(71) Applicant: Eyenovia, Inc., Tampa, FL (US)

(72) Inventors: Charles Eric Hunter, Boone, NC (US); Louis Thomas Germinario, Kingsport, TN (US); Jonathan Ryan Wilkerson, Raleigh, NC (US); Iyam Lynch, Boone, NC (US); Joshua Richard Brown, Hickory, NC (US)

(73) Assignee: Eyenovia, Inc., New York, NY (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/678,490

(22) Filed: Aug. 16, 2017

(65) Prior Publication Data

US 2018/0085251 A1 Mar. 29, 2018

Related U.S. Application Data

(63) Continuation of application No. 13/712,784, filed on Dec. 12, 2012, now abandoned.
(Continued)

(51) Int. Cl.
*A61M 35/00* (2006.01)
*A61F 9/00* (2006.01)
(Continued)

(52) U.S. Cl.
CPC .......... *A61F 9/0026* (2013.01); *A61F 9/0008* (2013.01); *B05B 17/0646* (2013.01); *B05B 17/0661* (2013.01); *B05B 17/0607* (2013.01)

(58) Field of Classification Search
CPC .............. A61F 9/0008; B05B 17/0646; B05B 17/0661
(Continued)

(56) References Cited

U.S. PATENT DOCUMENTS 1,482,747 A 2/1924 Howe
1,988,637 A 1/1935 Tinkham
(Continued)

FOREIGN PATENT DOCUMENTS

DE 19616300 10/1997
DE 199 34 582 1/2001
(Continued)

OTHER PUBLICATIONS

European Patent Office, International Search Report from PCT/US2012/069296, dated Mar. 20, 2013, 5 pages.
(Continued)

*Primary Examiner* — Andrew J Mensh
(74) *Attorney, Agent, or Firm* — Polsinelli PC

(57) ABSTRACT

An ejector device and method of delivering safe, suitable, and repeatable dosages to a subject for topical, oral, nasal, or pulmonary use is disclosed. The ejector device includes a housing, a reservoir disposed within the housing for receiving a volume of fluid, and an ejector mechanism in fluid communication with the reservoir and configured to eject a stream of droplets, the ejector mechanism comprising an ejector plate coupled to a generator plate and a piezoelectric actuator; the piezoelectric actuator being operable to oscillate the ejector plate, and thereby the generator plate, at a frequency and generate a directed stream of droplets.

8 Claims, 30 Drawing Sheets

Related U.S. Application Data

(60) Provisional application No. 61/591,786, filed on Jan. 27, 2012, provisional application No. 61/569,739, filed on Dec. 12, 2011.

(51) Int. Cl.
*B05B 17/00* (2006.01)
*B05B 17/06* (2006.01)
*B05B 1/08* (2006.01)
*B05B 3/04* (2006.01)
*A61M 11/06* (2006.01)

(58) Field of Classification Search
USPC .............................. 604/295; 239/102.2, 338
See application file for complete search history.

(56) References Cited

U.S. PATENT DOCUMENTS

| | | |
|---|---|---|
| 2,189,643 A | 2/1940 | Ward |
| 2,200,008 A | 5/1940 | Nowak |
| 2,249,608 A | 7/1941 | Greene |
| 2,322,808 A | 6/1943 | Hothersall |
| 2,552,857 A | 5/1951 | Knapp |
| 2,595,317 A | 5/1952 | White |
| 2,987,439 A | 6/1961 | Wittlinger |
| 3,170,462 A | 2/1965 | Hall |
| 3,187,757 A | 6/1965 | Jones et al. |
| 3,237,809 A | 3/1966 | Daragan et al. |
| 3,310,830 A | 3/1967 | Gattone |
| 3,314,426 A | 4/1967 | Caroll |
| 3,439,674 A | 4/1969 | Lelicoff |
| 3,602,399 A | 8/1971 | Litman et al. |
| 3,658,257 A | 4/1972 | Rood |
| 3,709,235 A | 1/1973 | Washburn et al. |
| 3,779,245 A | 12/1973 | Windsor |
| 3,780,950 A | 12/1973 | Brennan |
| 3,795,351 A | 3/1974 | Lehmann |
| 3,812,854 A | 5/1974 | Michaels et al. |
| 3,826,258 A | 7/1974 | Abraham |
| 3,845,764 A | 11/1974 | Windsor |
| 3,892,235 A | 7/1975 | Van Amerongen et al. |
| 3,901,443 A | 8/1975 | Mitsui et al. |
| 3,906,949 A | 9/1975 | Holland |
| 3,913,575 A | 10/1975 | Windsor |
| 3,934,585 A | 1/1976 | Maurice |
| 4,002,168 A | 1/1977 | Petterson |
| 4,012,798 A | 3/1977 | Liautaud |
| 4,052,985 A | 10/1977 | Coleman et al. |
| 4,067,499 A | 1/1978 | Cohen |
| 4,098,431 A | 7/1978 | Palmer et al. |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,388,343 A | 6/1983 | Voss et al. |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,533,082 A | 8/1985 | Maehara et al. |
| 4,543,096 A | 9/1985 | Keene |
| 4,544,570 A | 10/1985 | Plunkett et al. |
| 4,564,016 A | 1/1986 | Maurice et al. |
| 4,580,721 A | 4/1986 | Coffee et al. |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna et al. |
| 4,659,014 A | 4/1987 | Soth et al. |
| 4,679,551 A | 7/1987 | Anthony |
| 4,685,906 A | 8/1987 | Murphy |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikström |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,881,283 A | 11/1989 | Liautaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |
| 5,170,782 A | 12/1992 | Kocinski |

(56) References Cited

U.S. PATENT DOCUMENTS

| | | |
|---|---|---|
| 5,171,306 A | 12/1992 | Vo |
| 5,178,856 A | 1/1993 | Takahashi et al. |
| 5,193,745 A | 3/1993 | Holm |
| 5,201,726 A | 4/1993 | Kirkham |
| 5,203,506 A | 4/1993 | Gross et al. |
| 5,226,538 A | 7/1993 | Roselle |
| 5,252,318 A | 10/1993 | Joshi et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,296,673 A | 3/1994 | Smith |
| 5,299,739 A | 4/1994 | Takahashi et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,462,586 A | 10/1995 | Sugiyama et al. |
| 5,485,828 A | 1/1996 | Hauser |
| 5,496,411 A | 3/1996 | Candy |
| 5,499,751 A | 3/1996 | Meyer |
| D368,774 S | 4/1996 | Py |
| 5,515,841 A | 5/1996 | Robertson et al. |
| 5,518,179 A | 5/1996 | Humberstone et al. |
| 5,529,055 A | 6/1996 | Gueret |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A | 5/1997 | Rowe |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,881,956 A | 3/1999 | Cohen et al. |
| 5,893,515 A | 4/1999 | Hahn et al. |
| 5,894,841 A | 4/1999 | Voges |
| 5,938,117 A | 8/1999 | Ivri |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,008,468 A | 12/1999 | Tanaka et al. |
| 6,011,062 A | 1/2000 | Schneider et al. |
| 6,027,450 A | 2/2000 | Brown |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,135,427 A | 10/2000 | Tsai |
| 6,152,383 A | 11/2000 | Chen |
| 6,159,188 A | 12/2000 | Laibovitz et al. |
| 6,193,683 B1 | 2/2001 | Ludin et al. |
| 6,203,759 B1 | 3/2001 | Pelc et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,442,423 B1 | 8/2002 | Domb et al. |
| 6,443,146 B1 | 9/2002 | Voges |
| 6,467,476 B1 | 10/2002 | Ivri et al. |
| 6,526,976 B1 | 3/2003 | Baran |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,554,801 B1 | 4/2003 | Steward et al. |
| 6,569,131 B1 | 5/2003 | Michael et al. |
| 6,569,387 B1 | 5/2003 | Furner et al. |
| 6,601,033 B1 | 8/2003 | Melanson et al. |
| 6,601,581 B1 | 8/2003 | Babaev |
| 6,612,302 B1 | 9/2003 | Rand |
| 6,615,824 B2 | 9/2003 | Power |
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,659,364 B1 | 12/2003 | Humberstone et al. |
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | Della Vecchia et al. |
| 6,761,286 B2 | 7/2004 | Py et al. |
| 6,789,741 B2 | 9/2004 | Varanasi et al. |
| 6,814,071 B2 | 11/2004 | Klimowicz et al. |
| 6,851,626 B2 | 2/2005 | Patel et al. |
| 6,854,662 B2 | 2/2005 | Chen |
| 6,863,224 B2 | 3/2005 | Terada et al. |
| 6,877,642 B1 | 4/2005 | Maddox et al. |
| 6,885,818 B2 | 4/2005 | Goldstein |
| 6,901,926 B2 | 6/2005 | Yamamoto et al. |
| 6,913,205 B2 | 7/2005 | Cornet et al. |
| 6,921,020 B2 * | 7/2005 | Ivri .................. A61M 11/005 239/102.2 |
| 6,926,208 B2 | 8/2005 | Ivri |
| 6,946,117 B1 | 9/2005 | Schutt et al. |
| 6,964,647 B1 | 11/2005 | Babaev |
| 6,969,165 B2 | 11/2005 | Olsen |
| 6,974,450 B2 | 12/2005 | Weber et al. |

(56) References Cited

U.S. PATENT DOCUMENTS

| | | |
|---|---|---|
| 6,976,279 B1 | 12/2005 | Berke et al. |
| 6,976,969 B2 | 12/2005 | Messerly |
| 6,978,945 B2 | 12/2005 | Wong et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,081,757 B2 | 7/2006 | Unsworth et al. |
| 7,083,112 B2 | 8/2006 | Ivri |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |
| 7,314,187 B2 | 1/2008 | Hochrainer et al. |
| 7,316,067 B2 | 1/2008 | Blakey |
| 7,331,339 B2 | 2/2008 | Smith et al. |
| 7,357,133 B2 | 4/2008 | Goodchild |
| 7,472,701 B2 | 1/2009 | Pfichner et al. |
| D597,206 S | 7/2009 | Collins, Jr. et al. |
| 7,574,787 B2 | 8/2009 | Xu et al. |
| 7,678,089 B2 | 3/2010 | Py et al. |
| 7,712,466 B2 | 5/2010 | Addington et al. |
| 7,819,115 B2 | 10/2010 | Sexton et al. |
| 7,883,031 B2 | 2/2011 | Collins, Jr. et al. |
| 7,954,486 B2 | 6/2011 | Papania et al. |
| 8,012,136 B2 | 9/2011 | Collins, Jr. et al. |
| 8,485,503 B2 | 7/2013 | Lei |
| 8,545,463 B2 | 10/2013 | Collins, Jr. et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |
| 2002/0043262 A1 | 4/2002 | Langford et al. |
| 2002/0073989 A1 | 6/2002 | Hadimioglu |
| 2002/0074362 A1 | 6/2002 | Py et al. |
| 2002/0107492 A1 | 8/2002 | Brach et al. |
| 2002/0121285 A1 | 9/2002 | Poniatowski et al. |
| 2002/0124843 A1 | 9/2002 | Skiba et al. |
| 2002/0161344 A1 | 10/2002 | Peclat et al. |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1 | 2/2004 | Gonzalez et al. |
| 2004/0045547 A1 | 3/2004 | Yamamoto et al. |
| 2004/0050953 A1 | 3/2004 | Terada et al. |
| 2004/0082884 A1 | 4/2004 | Pal et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0215157 A1 | 10/2004 | Peclat et al. |
| 2004/0256487 A1* | 12/2004 | Collins, Jr. ......... A61M 11/005 239/338 |
| 2005/0001981 A1 | 1/2005 | Anderson et al. |
| 2005/0029307 A1 | 2/2005 | Py et al. |
| 2005/0077315 A1 | 4/2005 | Pavlu et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0199236 A1 | 9/2005 | Fink et al. |
| 2005/0240162 A1 | 10/2005 | Chen et al. |
| 2005/0244339 A1 | 11/2005 | Jauernig et al. |
| 2005/0261641 A1 | 11/2005 | Warchol et al. |
| 2005/0263608 A1 | 12/2005 | Ivri |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0243820 A1 | 11/2006 | Ng |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119968 A1 | 5/2007 | Collins, Jr. et al. |
| 2007/0119969 A1 | 5/2007 | Collins, Jr. et al. |
| 2007/0211212 A1 | 9/2007 | Bennwik |
| 2008/0017189 A1 | 1/2008 | Ruckdeschel et al. |
| 2008/0043061 A1 | 2/2008 | Glezer et al. |
| 2008/0097359 A1 | 4/2008 | Hochrainer et al. |
| 2008/0142624 A1 | 6/2008 | Ivri et al. |
| 2008/0164339 A1 | 7/2008 | Duru |
| 2008/0233053 A1 | 9/2008 | Gross et al. |
| 2008/0299049 A1 | 12/2008 | Stangl |
| 2008/0303850 A1 | 12/2008 | Shin et al. |
| 2008/0308096 A1 | 12/2008 | Borgschulte et al. |
| 2009/0025713 A1 | 1/2009 | Keller et al. |
| 2009/0114742 A1 | 5/2009 | Collins, Jr. |
| 2009/0149829 A1 | 6/2009 | Collins, Jr. |
| 2009/0167812 A1 | 7/2009 | Asai et al. |
| 2009/0192443 A1 | 7/2009 | Collins, Jr. et al. |
| 2009/0212133 A1 | 8/2009 | Collins, Jr. |
| 2009/0272818 A1* | 11/2009 | Valpey, III .......... B05B 17/0646 239/102.2 |
| 2010/0044460 A1 | 2/2010 | Sauzade |
| 2010/0211408 A1 | 8/2010 | Park et al. |
| 2010/0222752 A1 | 9/2010 | Collins, Jr. |
| 2010/0283601 A1 | 11/2010 | Tai et al. |
| 2011/0233302 A1 | 9/2011 | Chien-hua et al. |
| 2012/0143152 A1 | 6/2012 | Hunter et al. |
| 2013/0150812 A1 | 6/2013 | Hunter et al. |

FOREIGN PATENT DOCUMENTS

| | | |
|---|---|---|
| EP | 0011269 | 5/1980 |
| EP | 0150571 | 8/1985 |
| EP | 0224352 | 6/1987 |
| EP | 0389665 | 10/1990 |
| EP | 0 590 165 | 4/1994 |
| EP | 0 823 246 | 2/1996 |
| EP | 0 933 138 | 8/1999 |
| EP | 1493410 | 1/2005 |
| FR | 1271341 | 7/1961 |
| GB | 558866 | 7/1942 |
| GB | 1569707 | 7/1980 |
| JP | S62-142110 | 6/1987 |
| JP | H04-100557 | 4/1992 |
| JP | 10-506028 | 6/1998 |
| JP | 2005-324051 | 11/2005 |
| JP | 2008-515625 | 5/2008 |
| JP | 2008-168223 | 7/2008 |
| JP | 2009-072313 | 4/2009 |
| JP | 2012-508129 | 4/2012 |
| TW | I293898 | 7/1994 |
| TW | I293898 | 3/2008 |
| WO | 85/00761 | 2/1985 |
| WO | 91/12687 | 8/1991 |
| WO | 91/14468 | 10/1991 |
| WO | 94/13305 | 6/1994 |
| WO | 94/23788 | 10/1994 |
| WO | 95/15822 | 6/1995 |
| WO | 96/06581 | 3/1996 |
| WO | 97/05960 | 2/1997 |
| WO | 97/12687 | 4/1997 |
| WO | 98/19383 | 5/1998 |

(56) References Cited

FOREIGN PATENT DOCUMENTS

| WO | 99/17888 | 4/1999 |
|---|---|---|
| WO | 00/18455 | 4/2000 |
| WO | 00/66277 | 11/2000 |
| WO | 01/03645 | 1/2001 |
| WO | 01/58236 | 8/2001 |
| WO | 01/85245 | 11/2001 |
| WO | 02/28545 | 4/2002 |
| WO | 02/055131 | 7/2002 |
| WO | 2002/062488 | 8/2002 |
| WO | 02/072169 | 9/2002 |
| WO | 03/002045 | 1/2003 |
| WO | 03/002265 | 1/2003 |
| WO | 03/026556 | 4/2003 |
| WO | 03/097139 | 11/2003 |
| WO | 2004/028420 | 4/2004 |
| WO | 2004/050065 | 6/2004 |
| WO | 2004/103478 | 12/2004 |
| WO | 2004/105864 | 12/2004 |
| WO | 2006/006963 | 1/2006 |
| WO | 2006/082588 | 8/2006 |
| WO | 2008/015394 | 2/2008 |
| WO | 2009/148345 | 12/2009 |
| WO | 2011/083379 | 7/2011 |
| WO | 2012/009696 | 1/2012 |
| WO | 2012/009702 | 1/2012 |
| WO | 2012/009706 | 1/2012 |

OTHER PUBLICATIONS

European Patent Office, International Search Report from PCT/US2012/069309, dated Mar. 20, 2013, 5 pages.

"Alcon®: Sharing One Vision," 2009 Annual Report, 46 pages (2009).

Conover (Ed.), "View into the Future of Ophthalmology Treatments," *Healthcare Observer*, 1(8):2-37 (2009).

Dhand, "Nebulizers That Use a Vibrating Mesh or Plate with Multiple Apertures to Generate Aerosol," *Respir Care*, 47(12):1406-1418 (2002).

Donnelly et al., "Using ultrasonic atomization to produce an aerosol of micron-scale particles," *Review of Scientific Instruments*, 76:113301-1-113301-10 (2005).

Durnan et al., "Gold-Chlorine and Gold-Bromine Equilibria in Fused Salts," *The Journal of Physical Chemistry*, 68(4):847-850 (1964).

Galambos et al., "Drop ejection utilizing sideways actuation of a MEMS piston," *Sensors and Actuators A*, 141:182-191 (2008).

Hinds, *Aerosol Technology: Properties, Behavior, and Measurement of Airborne Particles*, pp. 42-71, 111-119, & 294-301 (1999).

Instruction Manual for Omron® Model NE-U03V MicroAir® Nebulizer, 20 pages (No date).

International Search Report dated Dec. 12, 2011, in International Application No. PCT/US2011/044291.

International Search Report dated Dec. 13, 2011, in International Application No. PCT/US2011/044286.

Product Description for Xalatan®: latanoprost ophthalmic solution, Pfizer Manufacturing, Belgium, NV, 8 pages (2009).

Quigley, "Improving Eye Drop Treatment for Glaucoma through Better Adherence," *Optometry and Vision Science*, 85(6):374-375 (2008).

Ranade et al., "Chapter seven: Intranasal and ocular drug delivery," *Drug Delivery Systems: Second Edition*, CLC Press, 39 pages (2004).

Rosen et al., "Printing High Viscosity Fluids Using Ultrasonic Droplet Generation," The George W. Woodruff School of Mechanical Engineering, Georgia Institute of Technology, pp. 239-253 (2008).

Shidhaye et al., "Novel drug delivery devices," *Pharma Times*, 38(7):24-27 (2006).

Tamilvanan et al., "The potential of lipid emulsion for ocular delivery of lipophilic drugs," *European Journal of Pharmaceutics and Biopharmaceutics*, 58:357-368 (2004).

Xia et al., "A potential application of a piezoelectric atomiser for ophthalmic drug delivery," *BOB*, 4(1):9-17 (2007).

Yee et al., "Trends in Glaucoma Treatment," EyeWorld Educational Symposium, San Francisco, 8 pages (2006).

Yuan et al., "MEMS-based piezoelectric array microjet," *Microelectronic Engineering*, 66:767-772 (2003).

Santvliet et al., "Determinants of Eye Drop Size," Survey of Ophthalmology, Mar.-Apr. 2004, vol. 49, pp. 197-211.

Brown et al., "The Preservation of Ophthalmic Preparations," Journal of the Society of Cosmetic Chemists, 1965, vol. 16, pp. 369-393.

\* cited by examiner

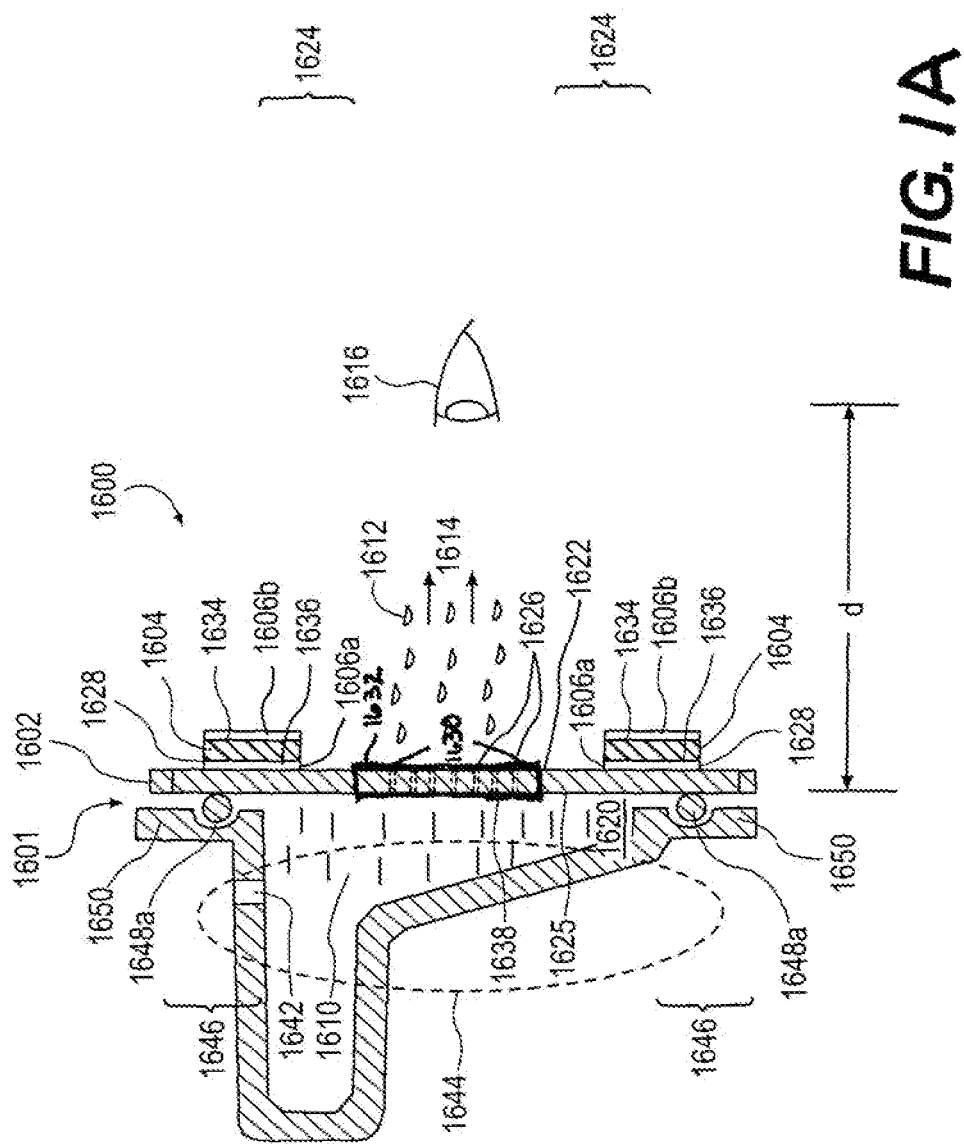

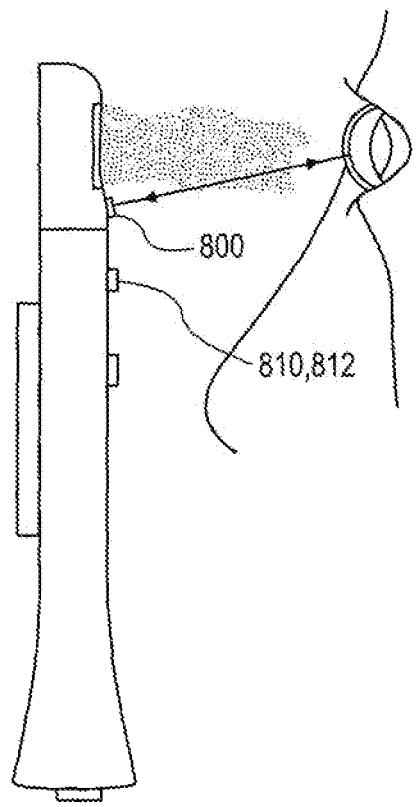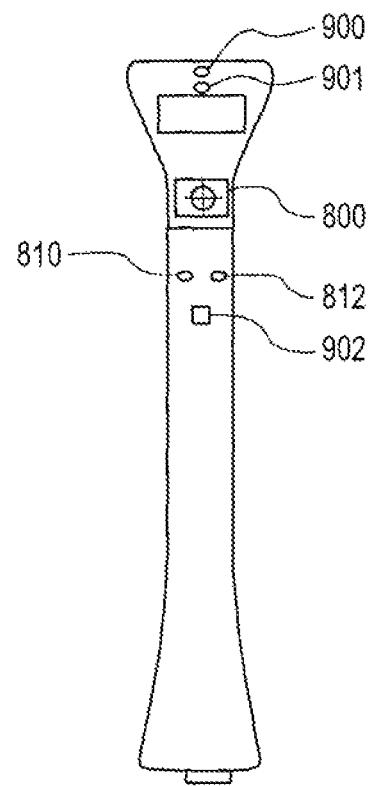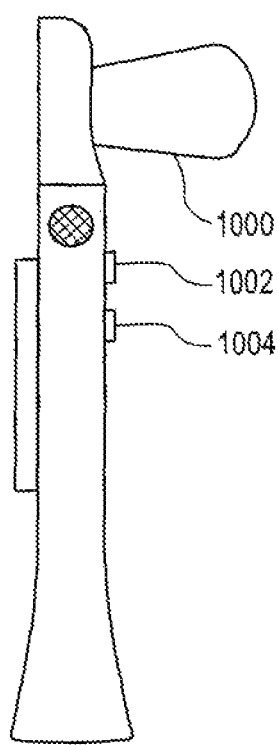
FIG. 4
FIG. 5
FIG. 6

METHODS TO LIGHT THE SURFACE OF EJECTOR

FIBER OPTIC CORD
(WITH ETCHED SURFACE)

SINGLE OR MULTIPLE
SURFACE MOUNTED LED(S)

LED RING

BIAS CUT FIBER OPTIC
CORD (WITH REFLECTIVE
LINNING)

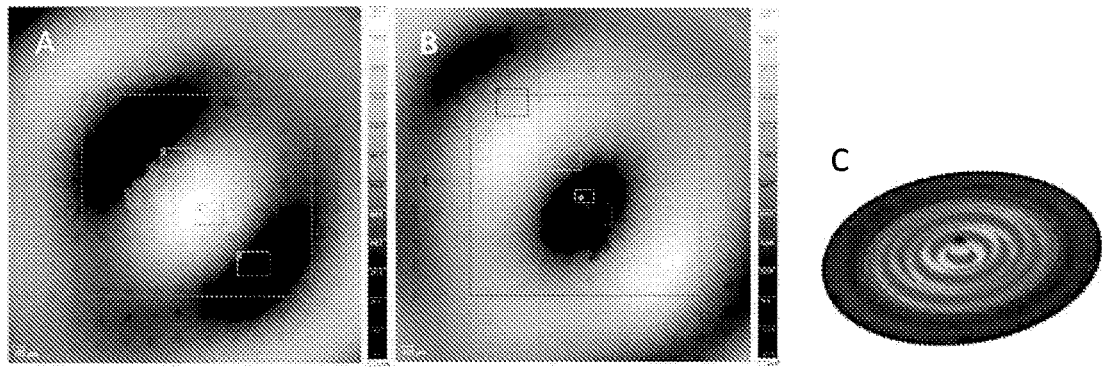
FIG. 20A  FIG. 20B  FIG. 20C
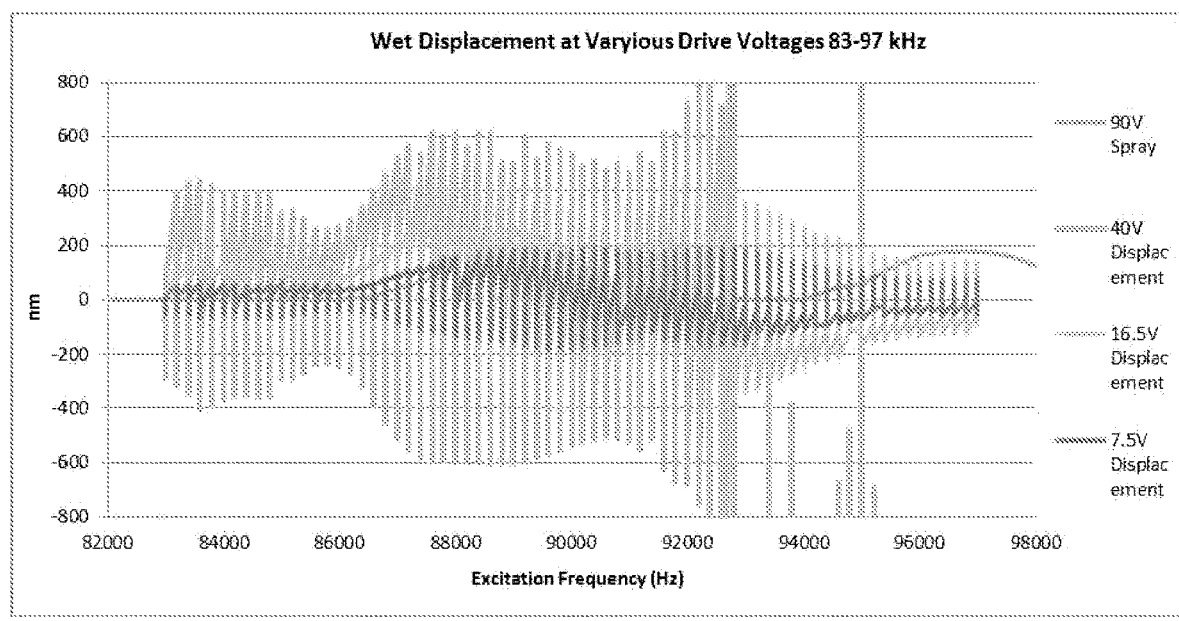
FIG. 21

EJECTOR MECHANISM, EJECTOR DEVICE, AND METHODS OF USE

RELATED APPLICATIONS

This application claims the benefit of the filing date of U.S. Provisional Application No. 61/569,739, filed Dec. 12, 2011, and of U.S. Provisional Application No. 61/591,786, filed Jan. 27, 2012, contents of which are herein incorporated by reference in their entireties.

BACKGROUND OF THE INVENTION

Using spray devices to administer products in the form of mists or sprays is an area with large potential for safe, easy-to-use products. A major challenge in providing such a device is to provide consistent and accurate delivery of suitable doses.

An important area where spray devices are needed is in delivery of eye medications. The application of fluids, as in the case of eye drops, has always posed a problem, especially for children and animals who tend to blink or jerk at the critical moment of administration, causing the droplet to land on the eyelid, nose or other part of the face. The impact of a large drop or drops of fluid on the eyeball, especially when the fluid is at a different temperature, also tends to produce a blinking reaction. Elderly also often lose the hand coordination necessary to get the eye drops into their eyes. Stroke victims have similar difficulties. Dropper delivery often requires a particular physical position, such as tilting of the head or a horizontal position, neither of which might be practical.

Often, it is important that the subject administer the correct dose the requisite number of times per day. However, in practice, subjects that are prescribed eye medications for home use tend to forget to dose, or dose excessively or cross-dose with other medications. One of the compliance problems is that, even if the subject is intent on following the treatment regimen, he or she may not be compliant for any number of reasons.

Currently, many of these medications are administered by eye droppers. Current eye drop devices often either require the head to be tilted back, the subject to lie down or provide downward traction on the lower eyelid, or a combination of traction and tilting, since the delivery mechanism typically relies on gravity for applying the medication. This is not only awkward, but involves a fair amount of coordination, flexibility and cooperation on the part of the subject to ensure that the medication gets into the eye while avoiding poking the eye with the dropper tip. Current eye dropper bottles pose the risk of poking the user in the eye, potentially causing physical damage to the eye, and further, exposing the tip to bacterial contamination due to contact with the eye. As such, the subject runs the risk of contaminating the medication in the eye drop bottle and subsequently infecting the eye. Additionally, a large volume of the medication flows out of the eye or is washed away by the tearing reflex. As a result, this method of administration is also inaccurate and wasteful. Moreover, the technology does not provide a satisfactory way of controlling the amount of medication that is dispensed, nor does it provide a way of ensuring that the medication that is dispensed actually lands on the eye and remains on the eye.

Eye droppers also provide no way of verifying compliance by a subject. Even if after a week of use the eye dropper bottle could be checked for the total volume of medication dispensed, e.g., by weighing the bottle, this does not provide a record of day-to-day compliance. A subject may have missed one or more doses and overdosed on other occasions. Also, the poor precision with which eye droppers deliver drops to the eye makes it difficult to determine whether the medication is actually delivered into the eye, even though it may have been dispensed.

Accordingly, there is a need for a delivery device that delivers safe, suitable, and repeatable dosages to a subject for ophthalmic, topical, oral, nasal, or pulmonary use.

SUMMARY OF THE INVENTION

The present disclosure includes an ejector device and method of delivering safe, suitable, and repeatable dosages to a subject for ophthalmic, topical, oral, nasal, or pulmonary use. The present disclosure also includes an ejector device and fluid delivery system capable of delivering a defined volume of fluid in the form of droplets having properties that afford adequate and repeatable high percentage deposition upon application.

The present disclosure includes and provides an ejector device for delivering a fluid to an eye of a subject, the device comprising a housing, a reservoir disposed within the housing for receiving a volume of fluid, an ejector mechanism configured to eject a stream of droplets having an average ejected droplet diameter greater than 15 microns, with the stream of droplets having low entrained airflow such that the stream of droplets deposit on the eye of the subject during use.

The disclosure further includes and provides an ejector mechanism configured to eject a stream of droplets, the ejector mechanism comprising: an ejector plate coupled to a generator plate and a piezoelectric actuator; the generator plate including a plurality of openings formed through its thickness; and the piezoelectric actuator being operable to oscillate the ejector plate, and thereby the generator plate, at a frequency and generate a directed stream of droplets. In certain implementations, the ejector plate has a central open region aligned with the generator plate, and the piezoelectric actuator is coupled to a peripheral region of the ejector plate so as to not obstruct the plurality of openings of the generator plate. The plurality of openings of the generator plate may be disposed in a center region of the generator plate that is uncovered by the piezoelectric actuator and aligned with the central open region of the ejector plate.

Another implementation of the disclosure provides a device for delivering a fluid to a target, the device comprising: a housing; a reservoir disposed within the housing for receiving a volume of fluid; and an ejector mechanism in fluid communication with the reservoir and configured to eject a stream of droplets, the ejector mechanism comprising an ejector plate coupled to a generator plate and a piezoelectric actuator. The generator plate includes a plurality of openings formed through its thickness; and the piezoelectric actuator is operable to oscillate the ejector plate, and thereby the generator plate, at a frequency and generate a directed stream of droplets.

Yet another implementation of the disclosure includes and provides for a method of delivering a volume of ophthalmic fluid to an eye of a subject, the method comprising ejecting a directed stream of droplets of an ophthalmic fluid contained in a reservoir from openings of an ejector plate, the droplets in the directed stream having an average ejecting diameter in the range of 5-2500 microns, including but not limited to 20-400 microns, 20-200, 100-200, etc., and an average initial velocity in the range of 0.5-100 m/s, 1-100 m/s, including but not limited to, 2-20 m/s.

BRIEF DESCRIPTION OF THE DRAWINGS

FIG. 1A shows a cross-sectional view of an implementation of an ejector assembly.

FIG. 1C-2 shows a schematic top view of an implementation of an active region of a generator plate.

FIG. 2 shows a three-dimensional view of an implementation of a housing of an ejector device.

FIG. 4 shows a side view of an implementation of an ejector device delivering medication to an eye.

FIG. 5 shows a front view of an implementation of FIG. 4.

FIG. 6 shows a side view of an implementation of an ejector device.

FIG. 20A-20C illustrates digital holographic images and a simulated image of axisymmetric modes of an exemplary ejector mechanism of the disclosure.

FIG. 21 illustrates displacement vs. applied drive voltage of an exemplary ejector mechanism of the disclosure.

DETAILED DESCRIPTION

Figure 1B:
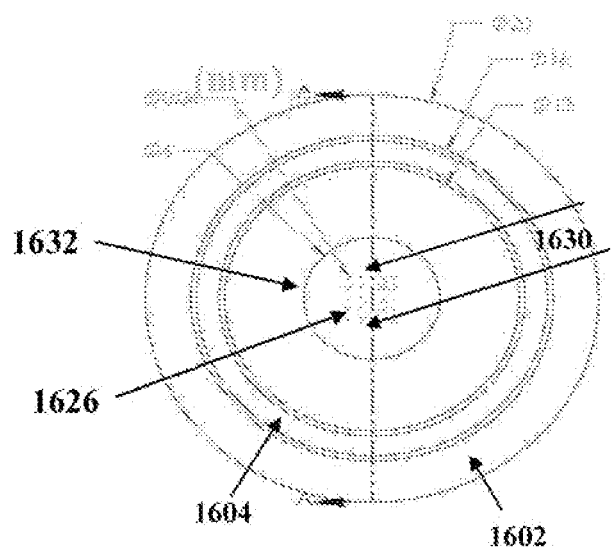
FIG. 1B shows a front view of an implementation of an ejector mechanism.

The present disclosure generally relates to ejector devices useful, e.g., in the delivery of fluid such as ophthalmic fluid to the eye. In certain aspects, the ejector devices include an ejector assembly including an ejector mechanism which generates a controllable stream of droplets of fluid. Fluid includes, without limitation, suspensions or emulsions which have viscosities in a range capable of droplet formation using an ejector mechanism. Exemplary ejector devices and related methods useful in connection with the present disclosure are described in U.S. application Ser. No. 13/184,484, filed Jul. 15, 2011, entitled "Drop Generating Device", U.S. application Ser. No. 13/184,446, filed Jul. 15, 2011, entitled "Ophthalmic Drug Delivery" and U.S. application Ser. No. 13/184,468, filed Jul. 15, 2011, entitled "Method and System for Performing Remote Treatment and Monitoring", which applications are each herein incorporated by reference in their entireties.

Certain aspects of the disclosure relate to an ejector device comprising an ejector mechanism including a generator plate having openings therethrough that is mechanically driven by a piezoelectric actuator and configured to eject a directed stream of droplets. The ability of such an ejection device to eject droplets is dependent on the ability of the piezoelectric actuator to mechanically drive and actuate the generator plate at sufficiently large displacements and at the desired optimum resonant frequency.

As explained in further detail herein, in accordance with certain aspects of the present disclosure, the ejector mechanism may form a directed stream of droplets which may be directed toward a target. The droplets may be formed in a distribution of sizes, each distribution having an average droplet size. The average droplet size may be in the range of about 15 microns to over 400 microns, greater than 20 microns to about 400 microns, about 20 microns to about 80 microns, about 25 microns to about 75 microns, about 30 microns to about 60 microns, about 35 microns to about 55 microns, about 20 microns to about 200 microns, about 100 microns to about 200 microns, etc. However, the average droplet size may be as large as 2500 microns, depending on the intended application. Further, the droplets may have an average initial velocity of about 0.5 m/s to about 100 m/s, e.g., about 0.5 m/s to about 20 m/s, about 0.5 to about 10 m/s, about 1 m/s to about 5 m/s, about 1 m/s to about 4 m/s, about 2 m/s, etc. As used herein, the ejecting size and the initial velocity are the size and initial velocity of the droplets when the droplets leave the ejector plate. The stream of droplets directed at a target will result in deposition of a percentage of the mass of the droplets including their composition onto the target.

As described herein, the ejector device and ejector mechanism of the disclosure may be configured to eject a fluid of generally low to relatively high viscosity as a stream of droplets. By way of example, fluids suitable for use by the ejector device can have very low viscosities, e.g., as with water at 1 cP, or less, e.g. 0.3 cP. The fluid may additionally have viscosities in ranges up to 600 cP. More particularly, the fluid may have a viscosity range of about 0.3 to 100 cP, 0.3 to 50 cP, 0.3 to 30 cP, 1 cP to 53 cP, etc. In some implementations, the ejection device may be used to eject a fluid having a relatively high viscosity as a stream of droplets, e.g., a fluid having a viscosity above 1 cP, ranging from about 1 cP to about 600 cP, about 1 cP to about 200 cP, about 1 cP to about 100 cP, about 10 cP to about 100 cP, etc. In some implementations, solutions or medications having the suitable viscosities and surface tensions can be directly used in the reservoir without modification. In other implementations, additional materials may be added to adjust the fluid parameter. By way of example, exemplary fluids are illustrated below:

| drugs/fluids | dynamic viscosity (cP) | kinematic viscosity (cP) | density |
|---|---|---|---|
| water | 1.017 | 1.019 | 0.99821 |
| Xalatan ™ | 1.051 | 1.043 | 1.00804 |
| Tropicamide | 1.058 | 1.052 | 1.00551 |
| Restasis ™ | 18.08 | 17.98 | 1.00535 |

Viscosity measured at 20° C.

Droplets may be formed by an ejector mechanism from fluid contained in a reservoir coupled to the ejector mechanism. The ejector mechanism and reservoir may be disposable or reusable, and the components may be packaged in a housing. The housing may be disposable or reusable. The housing may be handheld, miniaturized, or formed to couple to a base, and may be adapted for communication with other devices. Housings may be color-coded or configured for easy identification. Ejector devices, in some implementations, may include illumination means, alignment means, temperature control means, diagnostic means, or other features. Other implementations may be part of a larger network of interconnected and interacting devices used for subject care and treatment. The ejector mechanism may be, e.g., a piezoelectric actuator as described herein.

Figure 1C:
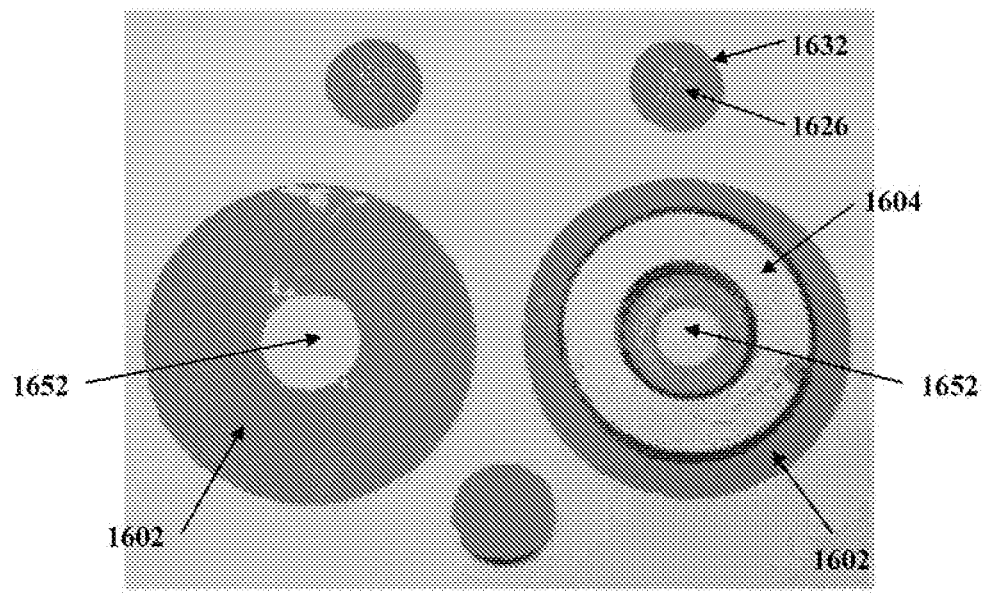
FIG. 1C shows an exploded view of an implementation of an ejector mechanism.

As discussed herein, in certain aspects, the ejector mechanism may comprise a piezoelectric actuator. Referring to FIGS. 1A-C, an ejector assembly 1600 may include an ejector mechanism 1601 and reservoir 1620. The ejector mechanism 1601 may include an ejector plate 1602 coupled to a generator plate 1632 including one or more openings 1626, that can be activated by a piezoelectric actuator 1604 which vibrates to deliver a fluid 1610, contained in a reservoir 1620, in the form of ejected droplets 1612 along a direction 1614. Again, the fluid may be an ophthalmic fluid that is ejected towards an eye 1616 of a human adult, child, or animal. Additionally, the fluid may contain an active pharmaceutical to treat a discomfort, condition, or disease of a human or an animal.

As shown in FIG. 1A, ejector plate 1602 is disposed over reservoir 1620 which contains fluid 1610. Surface 1625 of ejector plate 1602 is adjacent to the fluid 1610. Reservoir 1620 has open region 1638 which is adjacent to surface 1625 and to openings 1626. In this implementation, surface 1625 encloses the fluid 1610 in the reservoir 1620. The reservoir 1620 may be coupled to the ejector plate 1602 at a peripheral region 1646 of the surface 1625 of the ejector plate 1602 using a suitable seal or coupling. By way of example, the reservoir 1620 may be coupled via an O-ring 1648a. Although not shown, more than one O-ring can be used. As known in the art, the O-rings may have any suitable cross-sectional shape. Furthermore, other couplers such as polymeric, ceramic, or metallic seals can be used. Alternatively, the coupling can be eliminated altogether and reservoir 1620 may be integrally connected to ejector plate 1602, for example by welding or over molding. In such an implementation, an opening through which fluid is supplied to reservoir 1620 may be provided (not shown). Further still, the couplings may be made removable, such as a hinge, or may be made flexible or nonrigid connector, e.g., polymeric connector.

Other than the open region 1638, portions of the ejector plate 1602 may be covered by an additional reservoir wall 1650. In the implementation of FIG. 1A, wall 1650 does not directly contact the ejector plate 1602, rather it is coupled to O-rings 1648a. Alternatively, wall 1650 can be directly attached to ejector plate 1602. Furthermore, reservoir 1620 can be directly attached to ejector plate 1602 and wall 1650 can be omitted altogether.

The configuration of the reservoir 1620, including the shape and dimension, can be selected based on the amount of fluid 1610 to be stored, as well as the geometry of the ejector plate 1602. Alternative forms of reservoirs include gravity-fed, wicking, or collapsible bladders which operate under pressure differentials. These reservoirs may be pre-filled, filled using a micro-pump or by replacement of a cartridge. The micro pump may fill the reservoir by pumping fluid into or out of a collapsible or noncollapsible container. The cartridge may include a container which is loaded into the reservoir. Alternatively, the cartridge itself may be coupled to a disposable ejector assembly which is then replaced within the housing after a specified number of discharges. Exemplary reservoirs are illustrated in U.S. patent application Ser. No. 13/184,484, filed Jul. 15, 2011, the contents of which are herein incorporated by reference.

In some implementations, the reservoir 1620 includes through holes 1642 (only one shown in FIG. 1A) to allow air to escape from or enter the reservoir 1620 and keep the fluid 1610 in the reservoir at the appropriate ambient pressure. The through holes 1642 have a small diameter so that the fluid 1610 does not leak from the holes. Alternatively, no openings may be formed in the reservoir 1620, and at least a portion, e.g., the portion 1644, or the entire reservoir 1620 can be collapsible, e.g., in the form of a bladder. The entire reservoir may also be made in the form of a flexible or collapsible bladder. Accordingly, as the fluid 1610 is ejected through openings 1626, the reservoir 1620 changes its shape and volume to follow the changes in the amount of fluid 1610 in the reservoir 1620.

In the implementation of FIG. 1A, the ejector mechanism 1601 is activated by being vibrated by piezoelectric actuator 1604. Two electrodes 1606a and 1606b are formed on two opposite surfaces 1634 and 1636 of the piezoelectric actuator 1604 that are parallel to the surface 1622 of the ejector plate 1602 and activate the piezoelectric actuator 1604 to vibrate the ejector plate 1602 and a generator plate 1632 (described in further detail herein). The electrodes 1606*a* and 1606*b* can be attached to the ejector plate or piezoelectric actuator in any known manner including fixing by adhesive or otherwise bonding. They may also be overmolded in place to ejector plate 1602. Wires or other conductive connectors can be used to affect necessary electrical contact between ejector plate 1602 and the electrodes 1606*a* and 1606*b*. Alternatively, the electrodes may be formed on the ejector plate 1602 by plating or otherwise depositing. By way of example, the electrodes are attached by adhesive 1628 which is applied between the electrode 1606*a* and the ejector plate 1602. Electrode 1606*a* is in electrical contact with ejector plate 1602. When a voltage is applied across the electrodes 1606*a* and 1606*b*, the piezoelectric actuator 1604 deflects ejector plate 1602 and likewise generator plate 1632 to change shape to be more concave or convex.

An extensive range of voltages corresponding to different piezoelectric materials are known in the art, but by way of example, a voltage differential of between 5 and 60 V, 30 and 60 V, e.g., 40 or 60 V may be applied to the electrodes. When the direction of the voltage differential is reversed, for example to −40 or −60, the plate will deflect in the opposite direction. In this way, the piezoelectric actuator 1604 causes oscillation of ejector plate 1602 and generator plate 1632 which constitutes the vibration that results in formation of the droplets 1612 from fluid 1610. As the alternating voltage is applied to electrodes 1606*a* and 1606*b*, the ejector plate 1602 and the generator plate 1632 oscillate, causing the fluid droplets 1612 to accumulate in the openings 1626 and eventually be ejected from the openings 1626 along the direction 1614 away from the reservoir 1620. The frequency and wavelength of oscillation may depend on many factors, including but not limited to, the thickness, composition and morphology and mechanical properties of the ejector plate 1602, the volume of the openings 1626, the number of openings 1626, composition and structure of the piezoelectric actuator 1604, piezoelectric actuation driving voltage, frequency and waveform, the viscosity of the fluid, the stiffness of the ejector plate 1602, properties of the generator plate 1632, temperature and other factors. These parameters may be adjusted or selected to create the desired droplet stream. The frequency of droplet ejection also depends on many factors. In some implementations, the droplets 1612 are ejected at a frequency lower than the pulse frequency to the piezoelectric actuator 1604. For example, the droplets 1612 are ejected every 1-1000 cycles, and more specifically 8-12 cycles, of the ejector plate/generator plate vibration.

Without intending to be limited by theory, piezoelectric actuated generator plates possess a large number of eigenmodes that define the shape that the generator plate assumes when in motion, and the optimum eigenmode and shape provides the maximum displacement over the generator plate's active area. Exciting a given eigenmode requires placing the piezoelectric actuator at a given location relative to the standing wave of the generator plate. In this regard, the size and shape of a piezoelectric actuator, e.g., thickness, outer dimension and inner dimension, may determine, at least in part, its placement relative to the generator plate. Further, placement and bonding of the piezoelectric actuator on the generator plate may increase the generator plate stiffness. However, movement of the portion of the generator plate inside the inner dimension of the piezoelectric actuator is generally not restricted by placement of piezoelectric actuator.

In accordance with certain aspects of the disclosure, with reference to FIGS. 1B-1C, a first surface 1622 of ejector plate 1602 may be coupled to generator plate 1632. The ejector plate 1602 may generally comprise a central open region 1652 configured to align with the generator plate 1632. The generator plate 1632 may then be coupled with the ejector plate 1602 such that a center region 1630 of the generator plate 1632 aligns with the central open region 1652 of the ejector plate 1602. The center region 1630 of the generator plate 1632 may generally include one or more openings 1626, and alignment of the central open region 1652 of the ejector plate 1602 and the center region 1630 of the generator plate 1632 including the one or more openings 1626 allows for through communication of the one or more openings 1626.

In certain aspects, the central open region 1652 of the ejector plate 1602 may be smaller than the generator plate 1632 to provide sufficient overlap of material so as to allow for coupling of the ejector plate 1602 and the generator plate 1632. However, the central open region 1652 of the ejector plate 1602 should, in certain embodiments, be sized and shaped so as to not interfere with or obstruct the center region 1630 (and thereby one or more openings 1626) of the generator plate 1632.

By way of non-limiting example, the central open region 1652 of the ejector plate may be shaped in a manner similar to the generator plate 1632, and may be sized so as to have, e.g., about 0.5 mm to about 4 mm, about 1 mm to about 4 mm, about 1 mm to about 2 mm, etc., of overlap material available for coupling of the generator plate 1632 to the ejector plate 1602 (e.g., overlap on all sides). For instance, the central open region 1652 of the ejector plate may be shaped as a square, a rectangle, a circle, an oval, etc., in a manner to generally match the shape of the generator plate 1632, and sized such that the central open region 1652 is, e.g., about 0.5 mm to about 4 mm smaller in overall dimensions (i.e., the diameter of a circle is about 0.5 to about 4 mm smaller, the major and minor axis of an oval are about 0.5 to about 4 mm smaller, the length of the sides of a square or rectangle are about 0.5 to about 4 mm smaller, etc.).

In certain embodiments, the generator plate may be sized and shaped so as to have an overall outer dimension (OD) of about 4 mm to about 8 mm, e.g., 4 mm, 5 mm, 6 mm, etc. The ejector plate may be sized and shaped so as to have an overall outer dimension (OD) of about 18 mm to about 24 mm, e.g., 20 mm, 21 mm, 22 mm, 23 mm, etc., and an inner dimension (ID) (i.e., of the central opening) configured to provide sufficient overlap with the OD of the generator place. For instance, the ID of the ejector plate may be about 3 mm to about 16 mm, e.g., 4 mm, 6 mm, 12 mm, 14 mm, 16 mm, etc.

Generator plate 1632 may be coupled to ejector plate 1602 using any suitable manner known in the art including adhesive and bonding materials, e.g., glues, epoxies, bonding agents, and adhesives such as loctite E-30CL or Loctite 480 or 380 epoxies or other suitable super glue such as Loctite ultra gel, welding and bonding processing, e.g., ultrasonic or thermosonic bonding, thermal bonding, diffusion bonding, laser welding or press-fit etc.

Surface 1622 of ejector plate 1602 may be coupled to a piezoelectric actuator 1604, which activates generator plate 1632 to form the droplets upon activation. The manner and location of attachment of the piezoelectric actuator 1604 to the ejector plate 1602 affects the operation of the ejector assembly 1600 and the creation of the droplet stream. In the implementation of FIGS. 1B-C, the piezoelectric actuator 1604 may be coupled to a peripheral region of surface 1622 of plate 1602, while generator plate 1632 is coupled to surface 1622 so as to align with central open region 1652 of ejector plate 1602, as described above. Piezoelectric actuator 1604 is generally coupled to ejector plate 1602 so as to not cover or obstruct center region 1630 (and thereby one or more openings 1626) of the generator plate 1632. In this manner, fluid 1610 may pass through openings 1626 to form droplets 1612. In certain embodiments, the piezoelectric actuator may be shaped to generally correspond in shape with the generator plate. By way of example, the piezoelectric actuator may be sized to have an overall outer dimension (OD) of about 8 mm to about 24 mm, e.g., 8 mm, 10 mm, 12 mm, 14 mm, 16 mm, 18 mm, 19 mm, 20 mm, 21 mm, 22 mm, etc., and an inner dimension (ID) of about 4 mm to about 18 mm, e.g., 4 mm, 10 mm, 12 mm, 13 mm, 14 mm, 15 mm, 16 mm, etc.

As the ejector assembly 1600 is used for delivering therapeutic agents or other fluids to eyes, the ejector assembly 1600 may be generally designed to prevent the fluid 1610 contained in the reservoir 1620 and the ejected droplets 1612 from being contaminated. In some implementations, for example, a coating (not shown) may be formed over at least a portion of the exposed surface(s) of the piezoelectric actuator 1604, the ejector plate 1602, the generator plate 1632, etc. The coating may be used to prevent direct contact of the piezoelectric actuator 1604 and the electrodes 1606a and 1606b with the fluid 1610. The coating may be used to prevent interaction of the ejector plate 1602 or generator plate 1632 with the fluid, or it may be used to protect the piezoelectric actuator 1604 and electrodes 1606a and 1606b from the environment. For example, the coating can be a conformal coating including a nonreactive material, e.g., polymers including polyamide imide, polyether ether ketone (PEEK), polypropylene (PP), or high density polyethylene (HDPE), or an inert material selected from the group consisting of gold (Au), platinum (Pt), palladium (Pd), titanium nitride (TiN), chromium nitride (CrN), diamond like carbon (DLC)/amorphous carbon, nickel-platinum alloy, nickel-palladium alloy, platinum-palladium alloy, chromium carbon nitride, and aluminum (Al). Coatings are described in further detail herein.

The generator plate 1632 may be a perforated plate that contains at least one opening 1626. The one or more openings 1626 form the droplets as fluid 1610 is passed through. The generator plate 1632 may include any suitable configuration of openings, one configuration being depicted in FIG. 1B. By way of example, the openings may be formed as a grid, a spiral, or in a rectangular, rectilinear, or other pattern. The pattern may be regular or irregular. The pattern may maintain a uniform spacing of openings, or the spacing may be varied. For example, the density of openings may increase or decrease towards the center of the plate. The pattern may also cover all or part of the plate, i.e., center region 1632 may cover all or part of the generator plate, etc.

The openings 1626 may be formed in any suitable shape or volume, with an appropriate aspect ratio (i.e., height/thickness of opening vs. diameter of opening) selected and configured to efficiently eject droplets based, at least in part, on fluid properties. Without being limited by theory, higher aspect ratio openings produce a higher pressure gradient in the fluid being ejected, and therefore may be generally preferred for higher viscosity fluids. By way of example, in certain implementations, the generator plates may have openings with aspect ratios between about 1 and about 10, about 1 and about 5, about 1 and about 4, etc. Such aspect ratios may be obtained by varying opening height/thickness (i.e., generator plate thickness) and opening diameter. By way of example, opening diameter may range from about 20 μm to about 100 μm, about 20 μm to about 80 μm, about 20 μm to about 50 μm, about 30 μm to about 40 μm, etc. Opening height/thickness (i.e., generator plate thickness) may range from about 50 μm to about 500 μm, about 100 μm to about 200 μm, about 150 μm to about 200 μm, about 160 μm, etc. Selection of the aspect ratio of the openings may allow for formation of droplets of fluids having relatively high viscosities.

In certain implementations, the openings may have a generally cylindrical shape, that is, the diameter of the opening extending from surface 1622a of generator plate 1632 to surface 1625a of generator plate 1632 remains generally constant. In other implementations, with reference to FIG. 1K, the openings may have a generally fluted shape, i.e., wherein the diameter of the opening at surface 1622a is larger than the diameter of the opening at surface 1625A, and as the opening extends through generator plate 1632, the shape is tapered to form a microchannel. Nevertheless, the openings need not be limited to cylindrical or fluted shapes and may be tapered, conical, oval, hour glass, etc. See, e.g., FIGS. 1D-K. By way of example, a tapered opening may extend the entire thickness from surface 1622a to 1625a, or it may extend part way. The opening may also be beveled on one or both sides. The bevel may have an angled edge or a curved edge. The cross section of the opening may be round, or may have any other suitable shape. A few examples may be round, oval, fluted, rectangular or polygonal. The openings may be regularly shaped or irregularly shaped. The shape may be symmetric or asymmetric. The shape and aspect ratio of the openings may impact ejection of droplets, and may be optimized so as to efficiently eject fluids of varying viscosities, etc.

As indicated above, the size, shape, and aspect ratio of the openings 1626 affect the size and shape of the droplets and the droplet stream created by the ejector mechanism 1601. It may also affect the density distribution throughout the droplet stream. Thus, the size, shape, and aspect ratio of the openings as well as their pattern may be selected and configured to produce the desired properties of the droplet stream, based in part on fluid properties, in accordance with certain aspects of the present disclosure.

Figures 1, 1C, 2:
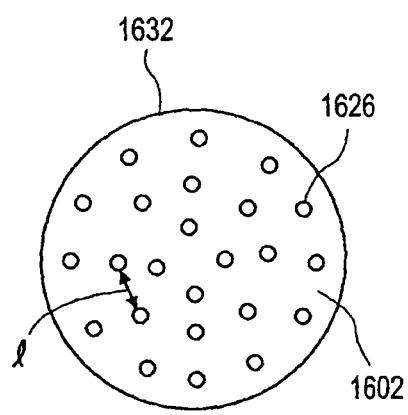
Figure 1D:
FIGS. 1D-1K show partial cross-sectional views showing examples of generator plate configurations.
Figure 1E:
Figure 1F:
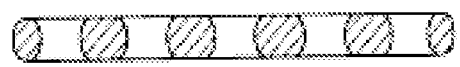
Figure 1G:
Figure 1H:
Figure 1I:
Figure 1J:
Figure 1K:
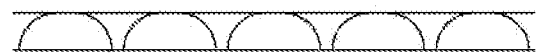

As with the size and shape of the openings 1626, the size and shape of the central region 1630 can be selected based on the desired properties of the droplet stream. As shown in FIG. 1C-2, by way of example, the openings 1626 are arranged in a circular pattern in the active region of generator plate 1632, but other patterns may also be used as explained above. The distance l between adjacent openings 1626 may be any suitable value, including 1 micron to a few mm, e.g., 150 microns to 300 microns. In one particular implementation, l is chosen to be 200 microns. Additionally, also as explained above, the separation of the openings 1626 need not be uniform.

Again, droplet stream generation depends on a complex interaction between fluid flow through openings, aspect ratios of openings, exit and entrance orifice diameter, entrance cavity geometry, generator plate material composition and mechanical properties, amplitude and phase of generator plate displacement, frequency of displacement of generator plate, and fluid properties such as viscosity, density, and surface energy, for example. For instance, without intending to be limited by theory, e.g., with reference to FIG. 1K, fluid flow rate in microchannels of a fluted opening is generally dependent on the pressure difference between the microchannel and exit face as described by the Young-LaPlace equation, divided by the resistance of the fluid flow within the microchannel. As such, the three-dimensional geometry of the microchannel and orifice dimensions of the openings of the generator plate can impact fluid flow rates through the openings.

$$Q = \Delta P / R$$

$$R = \frac{8 \mu L}{\pi r1 4}$$

$$\Delta P = \gamma \left( \frac{1}{r1} + \frac{1}{r2} \right)$$

$\mu$ = Fluid viscosity $L$ = Microchannel length $r1$ = Microchannel radius $\gamma$ = Fluid surface tension $r1$ = Microchannel radius $r2$ = Flute radius In some implementations, the length of the microchannel may be selected so as to optimize flow and ejected mass of fluid forming the droplet stream. By way of example, in fluted openings, the microchannels may range in length from 0 µm to about 150 µm, about 70 µm to about 150 µm, about 70 µm to about 120 µm, etc. In certain implementations, the microchannel may be between 120 µm and 150 µm, particularly for high viscosity fluids.

In some implementations, the ejector plate 1602 may be formed of a metal, e.g., stainless steel, nickel, cobalt, titanium, iridium, platinum, or palladium or alloys thereof. Alternatively, the plate can be formed of suitable material, including other metals or polymers such as polyether ether ketone (PEEK) or talc-filled PEEK, and be coated as described herein. The plate may be a composite of one or more materials or layers. The plate may be fabricated for example by cutting from sheet metal, pre-forming, rolling, casting, photoetching, laser cutting or otherwise shaping. The coatings may also be deposited by suitable deposition techniques such as sputtering, vapor deposition including physical vapor deposition (PAD), chemical vapor deposition (COD), or electrostatic powder deposition. The protective coating may have a thickness of about less than 0.1 µm to about 500 µm. It is desirable that the coating adhere to the ejector plate 102 sufficiently to prevent delamination when vibrating at a high frequency.

Referring to FIGS. 1B-C, in certain implementations, the ejector plate 1602 and generator plate 1632 may have concentric circular shapes. In certain aspects, the ejector plate may be larger than the generator plate, so as to accommodate coupling of the generator plate and other components (e.g., piezoelectric actuator, etc.) described herein. Likewise, in certain implementations, the generator plate 1632 may have a reduced size or diameter (in the implementation of a circular configuration) relative to the ejector plate 1602. In certain aspects, the overall size or diameter of generator plate 1632 may be, at least in part, determined by the size of center region 1630 and by the arrangement of openings 1626.

Figure 1L:
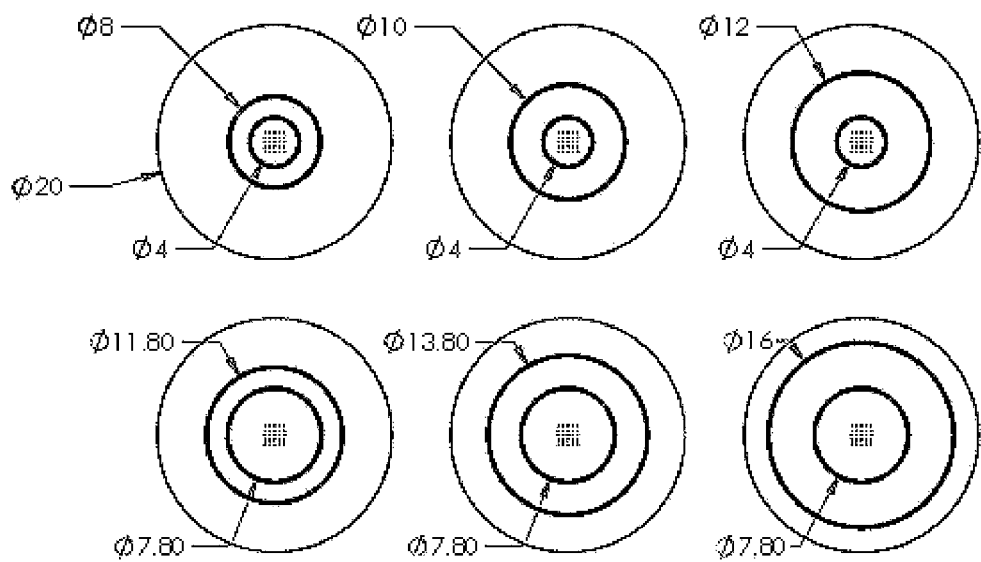
FIG. 1L-1M shows a front view of implementations of an ejector mechanism.
Figure 1M:
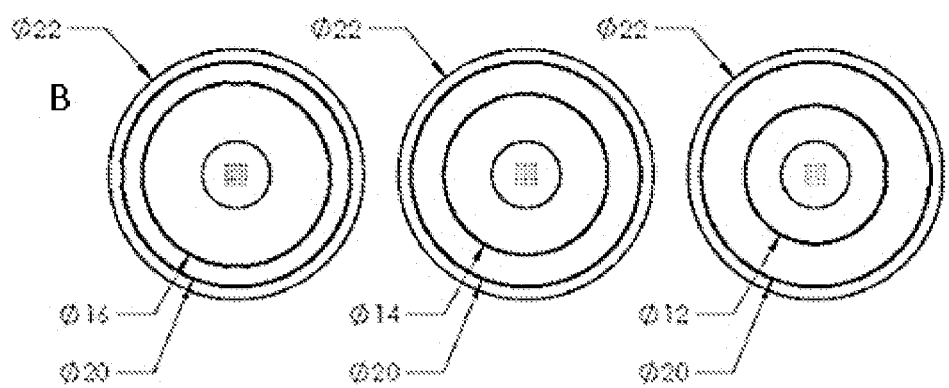
Figure 2:
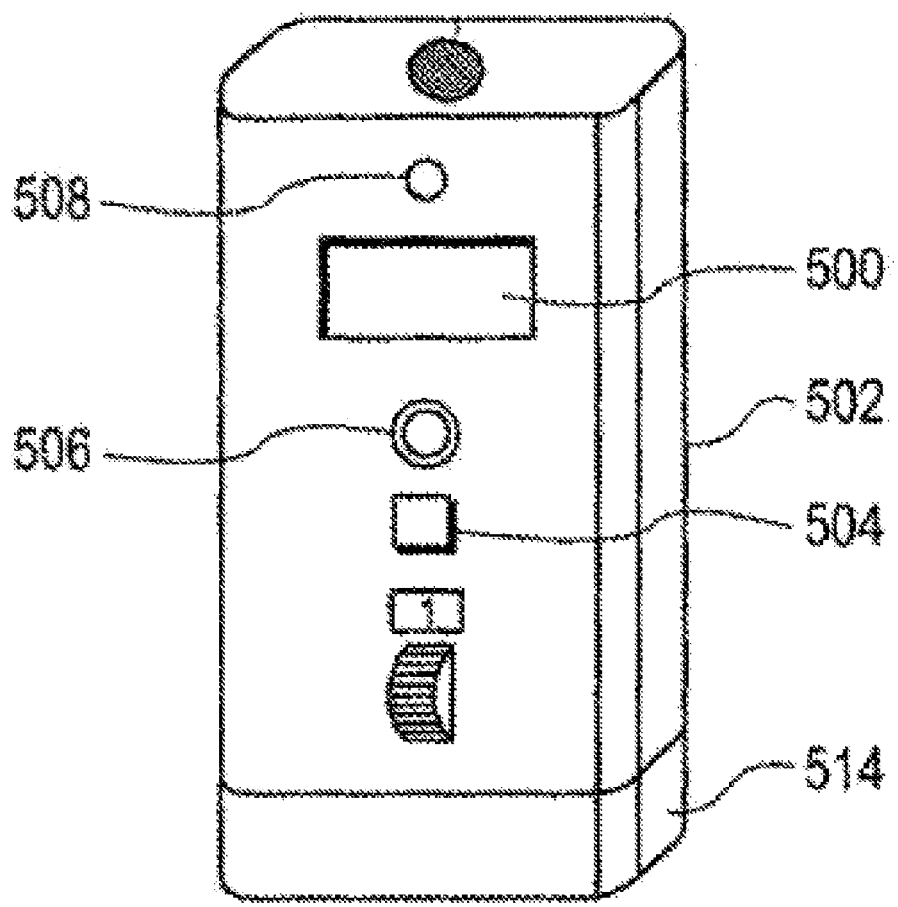

In other implementations, FIGS. 1L-M provide examples of concentric circular shapes with varying dimensions. FIG. 1L illustrates exemplary configurations having a 20 mm OD ejector plate, with generator plates and piezoelectric actuators of varying dimensions. FIG. 1M illustrates a configuration having a 22 mm OD, 4 mm ID, ejector plate, a 6 mm OD, generator plate, and piezoelectric elements of different outer and inner dimensions.

However, both plates may independently have other shapes, e.g., an oval, square, rectangular, or generally polygonal shape, and may be the same or different. Overall size and shape may be any suitable size and shape, and may be selected based on ejector device design parameters, e.g., size and shape of an outer device housing, etc. Additionally, the plates need not be flat, and may include a surface curvature making it concave or convex. The piezoelectric actuator 1604 may be of any suitable shape or material. For example, the actuator may have a circular, oval, square, rectangular, or a generally polygonal shape. The actuator 1604 may conform to the shape of the ejector plate 1602, generator plate 1632, or regions 1630/1652. Alternatively, the actuator 1604 may have a different shape. Furthermore, the actuator 1604 may be coupled to the ejector plate 1602 or surface 1622 of the ejector plate 1602 in one or more sections. In the example shown in FIGS. 1B-C, the piezoelectric actuator 1604 is illustrated in the shape of a ring that is concentric to the ejector plate 1602, generator plate 1632, and regions 1630/1652.

In some implementations, the generator plate 1632 may also be formed of a metal, e.g., stainless steel, nickel, cobalt, titanium, iridium, platinum, or palladium or alloys thereof, such as nickel-cobalt alloys. Alternatively, the plate can be formed of suitable material, including other metals or polymers such as ultrahigh molecular weight polyethylene (UHMWPE), polyimide (Kapton), polyether ether ketone (PEEK), talc-filled PEEK, polyvinylidine fluoride (PVDF), polyetherimide (Ultem), and be coated as discussed herein. The generator plate may be a composite of one or more materials or layers. The plate may be fabricated for example by cutting from sheet metal, pre-forming, rolling, casting, photoetching, laser cutting or otherwise shaping. The openings in the plate may be formed using suitable methods including but not limited to drilling by mechanical or optical means, such as laser drilling or ablation, or chemical processing, such as etching with or without stencils or lithographic patterning. The openings may also be pre-formed at the time of forming the plate using a UV LIGA process, which takes its name from the German expression, Lithographie (lithography) Galvanoformung (electroplating) Abformung (molding). By way of non-limiting example, a generator plate of the disclosure may be formed as described, e.g., in Lai et al., Influence of liquid hydrophobicity and nozzle passage curvature on microfluidic dynamics in a drop ejection process, *J. Micromech. Microeng.* 20 (2010) 015033.

The coatings may be pre-formed by dipping, plating, including electroplating, or otherwise encapsulating, such as by molding or casting. The coatings may also be deposited by suitable deposition techniques such as sputtering, vapor deposition, including physical vapor deposition (PAD) and chemical vapor deposition (COD), or electrostatic powder deposition. The protective coating may have a thickness of about less than 0.1 µm to about 500 µm. It is desirable that the coating adhere to the plate sufficiently to prevent delamination when vibrating at a high frequency.

In some implementations, the ejector plate 1602 and/or generator plate 1632 may be coated with a protective coating that is anti-contamination and/or anti-microbial. The protective coating can be conformal over all surfaces of the ejector plate and/or generator plate, including surfaces defining the openings 1626, portions of the openings (outer surface, inner surface, etc.). In other implementations, the protective coating can be applied over selected surfaces, e.g., the surfaces 1622, 1625, 1622a, 1625a, or surface regions, e.g., parts of such surfaces. The protective coating can be formed of a biocompatible metal, e.g., gold (Au), iridium (Ir), rhodium Rh), platinum (Pt), palladium (Pd), aluminum (Al) or alloys thereof, or titanium nitride (TiN), chromium nitride (CrN), amorphous carbon, or a biocompatible polymer, e.g., polyamide imide (PAI), polyether ether ketone (PEEK), polypropylene (PP), or high density polyethylene HDPE. Antimicrobial materials include metals such as silver, silver oxide, selenium or organic chlorides or organometallics such as alkylbenzyldimethylammonium (benzalkonium) chloride, or transition metal complexes of 1,1'-diacetylferrocene-derived thiocarbohydrazone, for example, or polymers such as carboxyl-containing ethylenecopolymers such as poly (ethylene-co-acrylic acid) (E/AA), and 8-hydroxyquinolinium ionomers. The protective coating can be in direct contact with the fluid 1610 or the droplets 1612. The coating may provide an inert barrier around the fluid or may inhibit microbial growth and sanitize the fluid 1610 and/or the droplets 1612.

Additionally, surface 1622 or 1622a of ejector plate 1602 or generator plate 1632 may be coated with a hydrophilic or hydrophobic coating. Additionally, the coating may be coated with a protective later. The surface may also be coated with a reflective layer. A coating layer may be both protective and reflective. Alternatively, the surface may have been formed to be reflective. For example, the surface may be made of stainless, nickel-cobalt, or other reflective material. A surface may have been formed or polished to be reflective. In addition to making the surface reflective, the surface may also be backlit on its surface or around its perimeter. In ophthalmic applications, a reflective surface aids the user in aligning the ejector assembly with the eye.

Piezoelectric actuator 1604 may be formed from any suitable material known in the art. By way of example, in some implementations, the piezoelectric actuator can be formed from lead zirconate titanate (Pb[Zr(x)Ti(1−x)]O3) (PZT), barium titanate (BaTiO3), bariumzirconate titanate (Ba(Zr,Ti)O3), BiFeO3-based ceramic, bismuth sodium titanate (BNT) material or a bismuth potassium titanate (BKT) material or polymer-based piezoelectric materials, such as polyvinylidine fluoride. The electrodes 1606a and 1606b can be formed of suitable conductors including gold, platinum, or silver. Suitable materials for use as the adhesive 1628 can include, but not be limited to, adhesives such as loctite E-30CL or Loctite 480 or 380 epoxies or other suitable super glue such as Loctite ultra gel, epoxies, silver-epoxy or nickel-epoxy paste. One example of a conductive adhesive includes an epoxy paste formulated using Ni powder and Loctite E-30CL. The reservoir 1620 may be formed of a polymer material, a few examples of which include Nexcel Latitude ML29xxC,Rollprint-ClearFoil V, low density and high density polyethylene (LDPE, HDPE), or ethylene vinyl acetate/polyvinylidene chloride (EVA/PVDC) coextruded films.

In certain aspects of the disclosure, the ejector mechanism may be configured so as to facilitate actuation of the ejector plate, and thereby the generator plate, by the piezoelectric actuator. As described above, the generator plate may be configured to optimize ejection of a fluid of interest. For example, the aspect ratio of the openings of the generator plate may be selected based, in part, on fluid properties, such that the general thickness of the generator plate ranges from about 50 μm to about 500 μm, as described above.

Without being limited by theory, in certain implementations, direct actuation of a relatively thick generator plate, though possible, may be less optimal. As such, in certain implementations, actuation of the ejector mechanism may be optimized using configurations including a generator plate coupled to an ejector plate, as described herein. In addition, reducing the surface area of the generator plate (i.e., the central region having one or more openings) likewise reduces manufacturing costs, reduces potential related manufacturing defects, and increases manufacturing efficiencies and output. In certain aspects, the ejector plate may be sized and shaped in a manner to facilitate actuation of the ejector mechanism (i.e., actuation of the ejector plate and thereby the generator plate). By way of example, configurations of the ejector plate may effectuate actuation of the ejector mechanism though selection of properties (e.g., size, shape, material, etc.) that facilitate flex of the ejector plate, and thereby vibration of the generator plate. For instance, the ejector plate may have a thickness generally ranging from about 10 μm to about 400 μm, from about 20 μm to about 100 μm, from about 20 μm to about 50 μm, about 30 μm to about 50 μm, etc. Again, without being limited by theory, in certain implementations, direct actuation of a relatively thinner ejector plate (compared to the generator plate), may be more optimal.

In accordance with certain implementations of the disclosure, the configuration of the ejector plate and the generator plate may be selected such that the center region of the generator plate including openings (e.g., the "active region" of the generator plate) produces a symmetric oscillation with a normal mode of oscillation. Without being limited by theory, in certain implementations, configurations of the ejector plate and generator plate may be selected such that 0,2 normal mode and 0,3 normal mode of oscillation of the active region of the generator plate is observed. The mode is associated with a maximum amplitude and displacement of the active region, wherein the mode is designated as (d,c) where d is the number of nodal diameters and c is the number of nodal circles.

The magnitude and frequency of the ejector plate vibration can also be controlled by controlling the voltage pulses applied to the electrodes 1606a, 1606b, e.g., a voltage differential of 40 or 60 V may be applied to the electrodes. As discussed above, the pulses are created by voltage differentials that deflect ejector plate 1602, and thereby generator plate 1632. In some implementations, one of the electrodes 1606a or 1606b is grounded and voltage pulses, e.g., bipolar pulses, are applied to the other one of the electrodes 1606a or 1606b e.g., to vibrate the ejector plate 1602. By way of example, in one implementation, the piezoelectric actuator 1604 can have a resonant frequency of about 5 kHz to about 1 MHz, about 10 kHz to about 160 kHz, about 50-120 kHz to about 50-140 kHz, etc., e.g., 108-130 kHz. The applied voltage pulses can have a frequency lower, higher, or the same as the resonant frequency of the piezoelectric actuator 1604.

In certain implementations, delivery time of the droplets is about 0.1 ms to about several seconds. Without wishing to be bound by theory, it is believed that human eyes take about 300 ms to about 400 ms between blinks. Therefore, for implementations where delivery is desired to be between blinks, the delivery time may be about 50 ms to about 300 ms and more particularly 25 ms to 200 ms. In one implementation, the delivery time is 50 ms to 100 ms. In this way, the ejected droplets can be effectively delivered and deposited in the eye during a blinking cycle of the eye. In some implementations, for example over-the-counter saline dispensers, the delivery time can be as long as several seconds, e.g., 3-4 seconds, spanning several blink cycles. Alternatively, a single delivery can be administered by several bursts or pulses of droplet ejection. Additionally, and not intending to be limited by theory, pulsing may be used to reduce the peak amplitude of the droplet airstream by spreading the impulse out over time. Therefore, the pressure of the ejection on the target may be mitigated. Furthermore, pulsing may also reduce droplet agglomeration and result in less entrained air generation. By way of example, pulses of 25 ms can be administered with stop times of 25 ms separating the pulses. In one implementation, the pulses may be repeated for a total of 150 ms total time.

The ejector assembly described herein may be incorporated into an ejector device. Exemplary ejector devices are illustrated in U.S. patent application Ser. No. 13/184,484, filed Jul. 15, 2011, the contents of which are herein incorporated by reference. By way of non-limiting example, one implementation of an ejector device is shown in FIG. 2. It shows an ejector mechanism 500 housed in a housing 502. The housing 502 includes a hand-actuated trigger 504, an eye-sensor 506 in the form of a CCD array or near infrared (NIR) or other sensor to detect an eyeball or the retina of the eye, a light source 508 (in this case a focused light-emitting diode (LED) providing a low intensity light substantially along the ejection path of the ejected fluid droplets), and a reservoir 514, which in this case is releasably attached to the housing 502 and is in flow communication with the ejector mechanism 500. The reservoirs can be refillable, allowing the rest of the applicator to be refillable.

Figure 3:
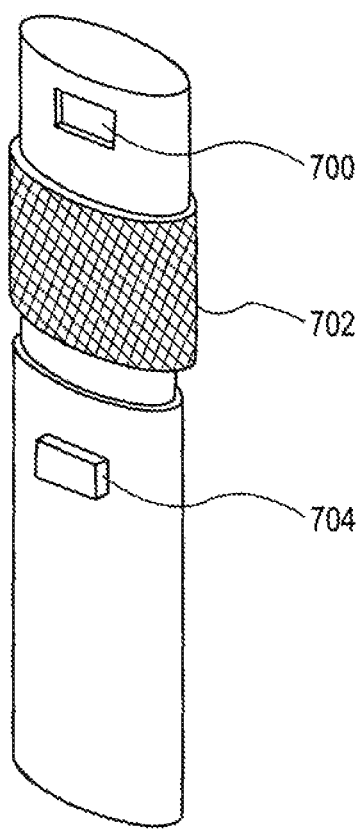
FIG. 3 shows a three-dimensional view of an implementation of a housing of an ejector device.

Another implementation of an ejector device is shown in FIG. 3. In this implementation the fluid is dispensed using ejector mechanism 700. A cover 702 is shown in its retracted position but is movable to a closed position by sliding the cover 702 upward so as to cover the ejector mechanism 700. A button 704, which can be thumb-activated, controls the dispensing of the fluid. This implementation may also be implemented as a disposable device, as well as portions of it may be disposable. For example, a replaceable reservoir or cartridge can be used. In practice a user may attach the reservoir 514 to the housing, e.g., if the reservoir is disposable and requires replacement.

The device can be pointed at the target, for example, a human or animal eye, using an eye sensor, e.g., an LED (not shown) to help in correctly aligning the applicator. Once the eye-sensor detects an eye, it sends a signal to a controller/processor, which in turn activates the ejector mechanism. One implementation of the device which could be embodied in any of the implementations may include an ejector mechanism and LED that turns on when the device is switched on, for example, by a power switch or by lifting the device out of a docking station. The light from the LED is shone onto the target, e.g., the subject's eye, to correctly target the eye prior to dispensing fluid. The device may include a rest, support, or spacer to aid in alignment as discussed below.

Other implementations to ensure correct alignment of the device with the eye are also contemplated. These implementations, examples of which are shown in FIGS. 4-12H may be formed as handheld or palmheld units and can be miniaturized to a further extent for additional applications. In one implementation, shown in FIGS. 4 and 5, a mirror 800 is provided on the housing for reflecting an image of the user's eye back into the user's eye when the device is correctly aligned with the eye. In this implementation a cross-hair is provided on the mirror, as shown in the front view of FIG. 5, to help the user centralize the device for ejection of fluid into the eye. The implementation of FIGS. 4 and 5 also includes an LED 810 to alert the user when a dose is due and a second LED 812 to light up when a full dose has been delivered.

FIG. 5 shows another implementation. An infra-red transmitter 900 (e.g., IR LED) and infra-red (IR) photo detector 901 are mounted on the front surface of the device to transmit an infra-red beam or pulse, which is received by an IR photo detector 902 when the device is correctly aligned with the eye and the IR beam or pulse is reflected off the eye.

Yet another implementation of the invention is shown in FIG. 6, which makes use of a conical sleeve 1000 to position the eye relative to the ejector mechanism. The sleeve 1000 can, for example, be implemented as a rubber or silicon hood, and may serve the additional function of providing a shaded or darkened imaging zone for imaging the eye with a scanner or camera. A button 1002 is mounted on the device for triggering the ejection of the fluid, and a second button 1004 serves to trigger an image capturing device (not shown) mounted on the device under the sleeve 1000.

Figure 7:
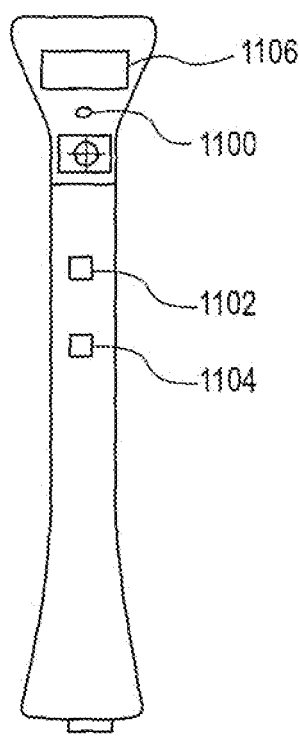
FIG. 7 shows a front view of an implementation of an ejector device.

FIG. 7 shows another implementation a low intensity light beam e.g., light emitting diode (LED) 1100 emits a beam when button 1102 is depressed. The light beam is configured to shine into the user's eye when the ejector mechanism 1106 or other fluid dispenser of the device is correctly aligned with the eye, as shown by the implementation of FIG. 7. This implementation does not have a camera for capturing an image of the eye, but serves simply to dispense fluid, e.g., a flushing fluid or medication into the eye by depressing a button or switch 1104. The button 1104, e.g., sends a signal to actuate the ejector mechanism.

Figure 8:
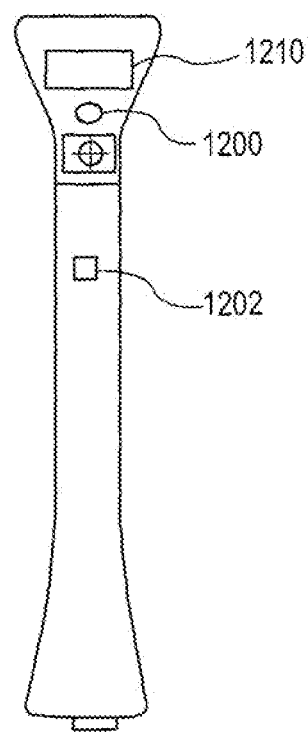
FIG. 8 shows a front view of an implementation of an ejector device.

In FIG. 8, an image capture device, including cameras, scanners, or other sensors without limitation, e.g. charge coupled device (CCD), 1200, may be provided to detect the presence of an eye and to ensure that the eye is open. The eye sensor provides control information, which in one implementation provides a controlling signal to a controller or processor in the device for controlling the ejection of fluid. Thus, a processor is included in such implementations to control the activation of the ejector mechanism to eject fluids only when the camera image indicates that the eye or a pre-defined area of the eye is correctly aligned with the fluid applicator. The device can readily take into account the delay between the signal from the camera and the ejection of droplets from the device and can time delivery to beat the blink cycle.

The lighting mechanisms described herein, e.g., LEDs, may be in ranges above 280 nm, including, e.g., 290-1600 nm, wavelengths for illuminating the target. Any suitable implementation may be used to provide for the lighting mechanism. Exemplary lighting mechanisms are illustrated in FIGS. 9A-D, including fiber optic cords, surface mounted LEDs, LED rings, etc. The lighting mechanism may be operable to pulse the light for different periods of time, e.g., 120 nanoseconds (ns) to limit pupil reaction and permit analysis of the eye with different frequency optical detectors, scanners, or cameras as explained above. Furthermore, the device may include an adaptive optics chip to perform wavefront correction for clearer images. The device may also include a fixation source e.g., an LED or LED pattern to define a moving eye-focusing image and assist with pediatric usage. This also serves to move or rotate the eyeball during application of medication to assist in spreading the medication across the corneal surface.

After the device is turned on, the ejector mechanism can be triggered. An activation trigger may serve as the triggering mechanism of the ejector mechanism, subject to control by a controller in the ejector device. The button may be any suitable means to turn on a device including electrical and mechanical activation triggers, pushbuttons, levers, slide switches, tactile switches including momentary switches, pressure pads, motion sensors, magnetic and Hall effect switches, electrostatic switches, resistive or capacitive touch switches, Reeves switches, switches operated by infra-red, radio frequency, light, or sound detectors, or timers or internal activation signals. The activation may be local or remotely controlled.

Some implementations may include a watchdog timer which monitors the ejector device to ensure proper operation. In another implementation, the device may sense the presence of the droplet stream for self-diagnostic purposes and to confirm proper operation. By way of example, one or more light emitters, e.g., LED, laser diode, may be used to shine light against the droplet stream. In one implementation, the light may be shown perpendicularly to the stream. A device may include, in one implementation, light detectors, e.g., photo detector, which may be used in conjunction with a shone light to detect reflection and refraction, such as reflection of the shone light off of the stream, and use this detection to determine proper operation of the device. A system may further react in response to the detection and determination of proper operation, e.g., by alerting a compliance agent or system that the device may not be properly functioning.

In the implementation of FIG. 8, the device also includes a hand operated trigger 1202, however, in this implementation the ejection is subject to correct positioning of the ejector mechanism 1210 relative to the eye as defined by the image information obtained from the camera 1200.

Figure 10A:
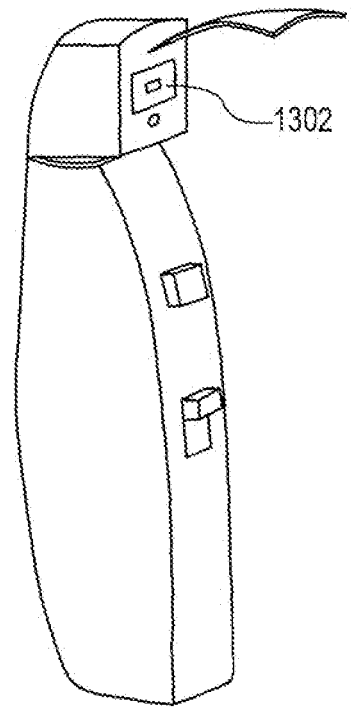
FIGS. 10A-10B show an implementation of an ejector device including a spacer.
Figure 10B:
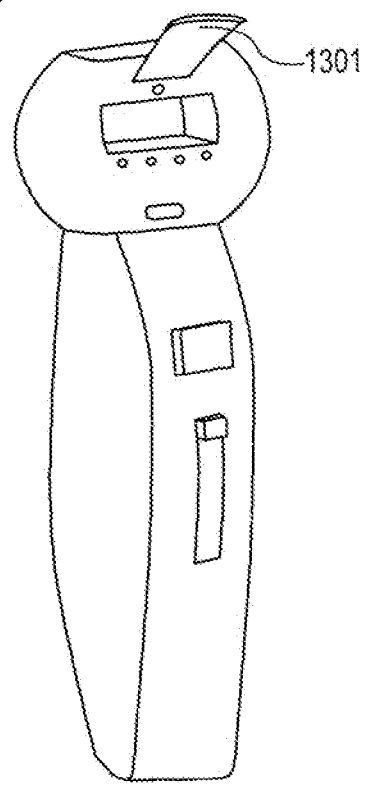
Figure 9A:
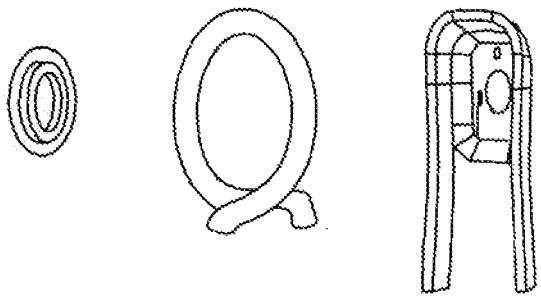
FIGS. 9A-9D show implementations including lighting mechanism features.
Figure 9B:
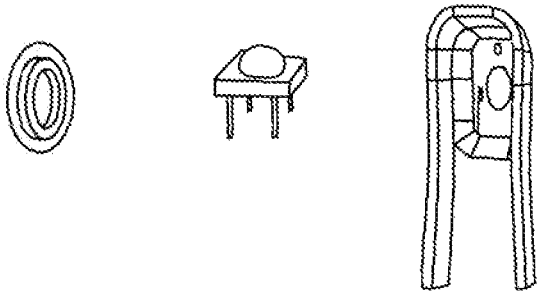
Figure 9C:
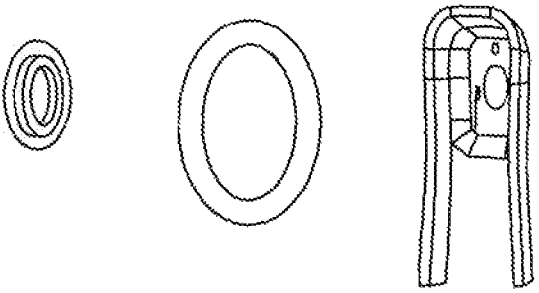
Figure 9D:
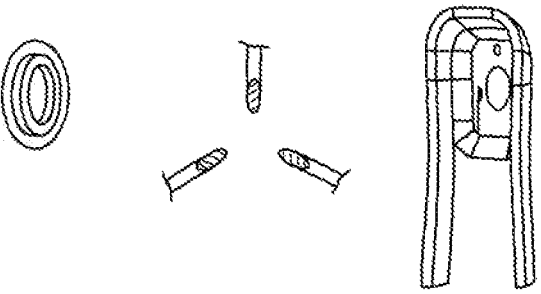

FIGS. 10A and 10B show another implementation depicting a hinged cover. The device shown in FIG. 10B also includes a removable reservoir 1300, which allows both the reservoir and ejector to be discarded once the fluid in the reservoir is depleted. Cover 1301 flips down to provide a cover for the ejector. This protects the ejector mechanism when not in use or in transport. Also, by engaging with a peripheral seal 1302, the cover 1301 reduces evaporation of fluid. Cover 1301 can also be used as a spacer or rest to rest against, for example, the eyebrow, to align the device against the target, for example the eye.

Figure 11A:
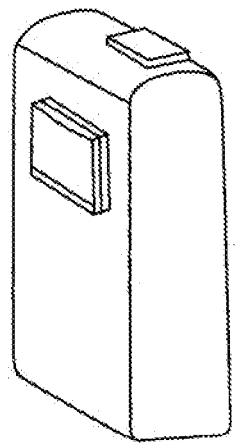
FIGS. 11A-11B show an implementation of an ejector device including a spacer.
Figure 11B:
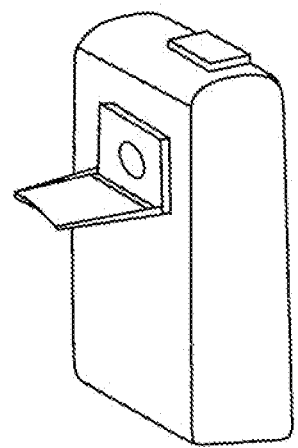
Figure 12A:
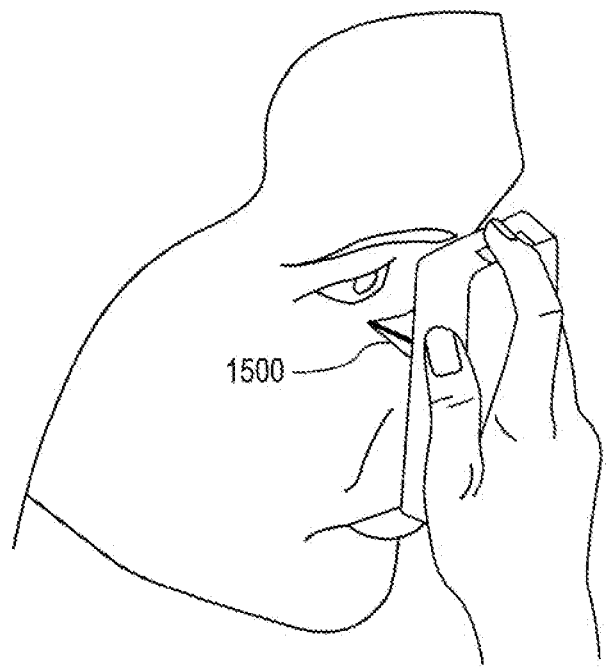
FIG. 12A shows an implementation of the device including a spacer.
Figure 12:
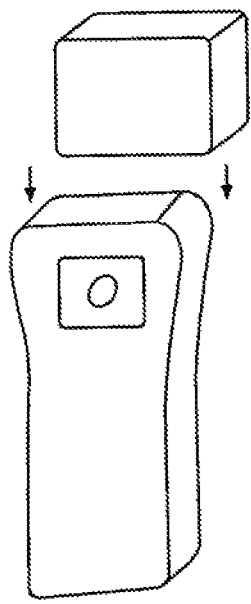
FIGS. 12B-12H show exemplary covers.
Figure 12:
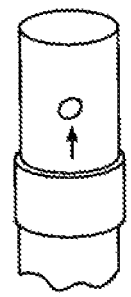
Figure 12:
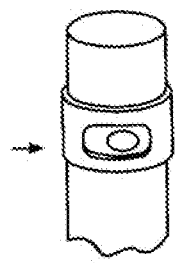
Figure 12:
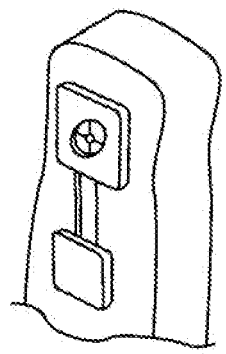
Figure 12:
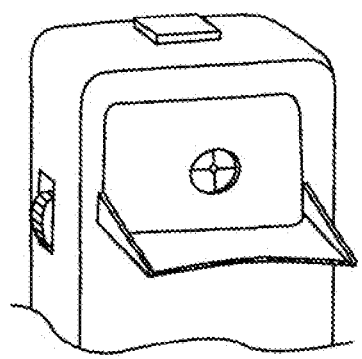
Figure 12:
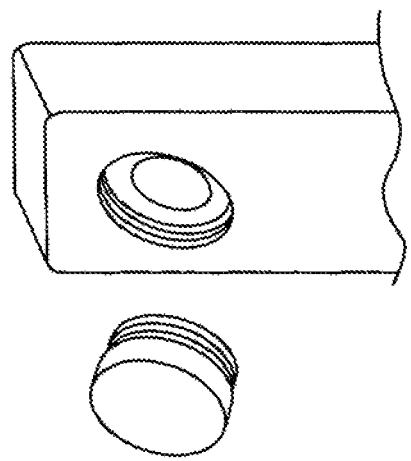
Figure 12:
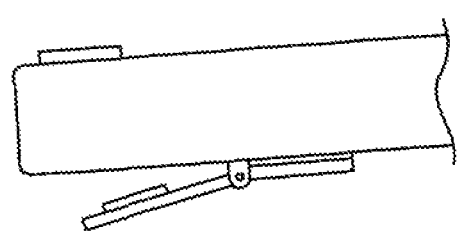

The cover may also hinge up as shown in FIGS. 11A and 11B. A spacer may also be formed as a separate or integral piece on the exterior of the device as depicted by 1500 in FIG. 12A. The spacer rests against a portion of the anatomy to aid in alignment of the device with the target. In addition to the noted covers, the cover may be omitted. Additionally, the cover can be of any suitable mechanism, including iris-type closure, covers that slide from left to right, cover that are coupled via a friction fit, in a threaded manner, louvered, or clipped on. The cover can be coupled with any suitable mechanical, magnetic, or electromechanical means. For disposable packages, the cover may be an exterior or protective wrapping or covering. Additionally, the cover may be sealed against the ejection area with a leaf spring or other polymeric seal. This seal can be made of a suitable polymer, for example, polypropylene, polyethylene, high density polyethylene or teflon. Furthermore, other seals such as ceramic sealers, metallic sealers, or gaskets can be used to seal the cover against the housing. FIGS. 12B-H show several alternative implementations of covers.

Figure 13B:
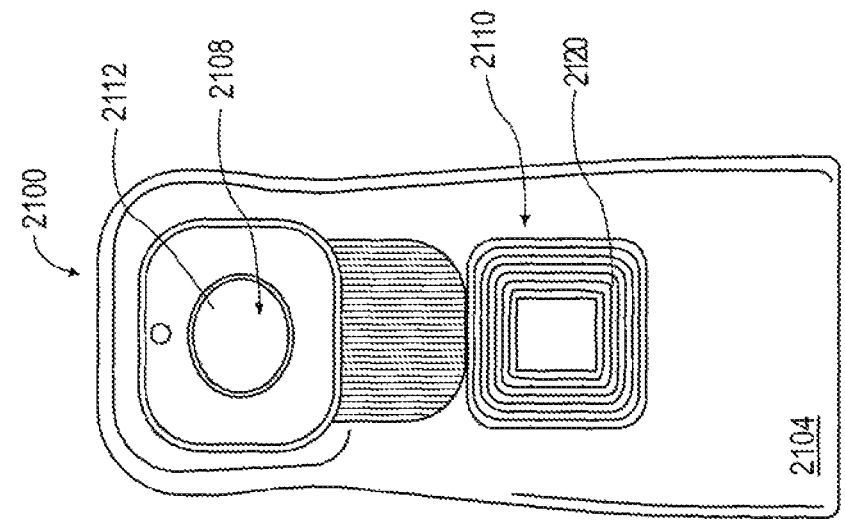
FIG. 13B shows an implementation of an ejector device with a slide cover opened.
Figure 13A:
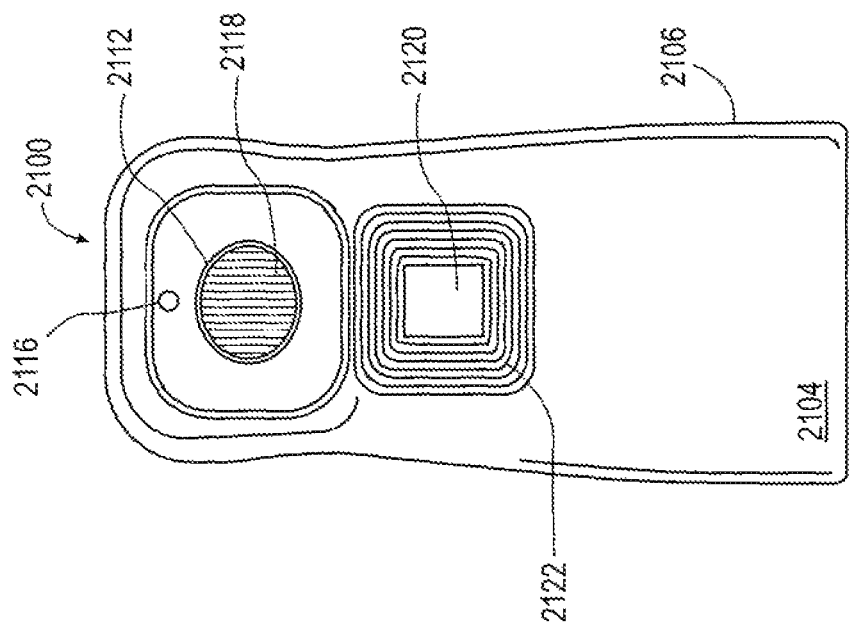
FIG. 13A shows an implementation of an ejector device with a slide cover in the closed position.
Figure 13D:
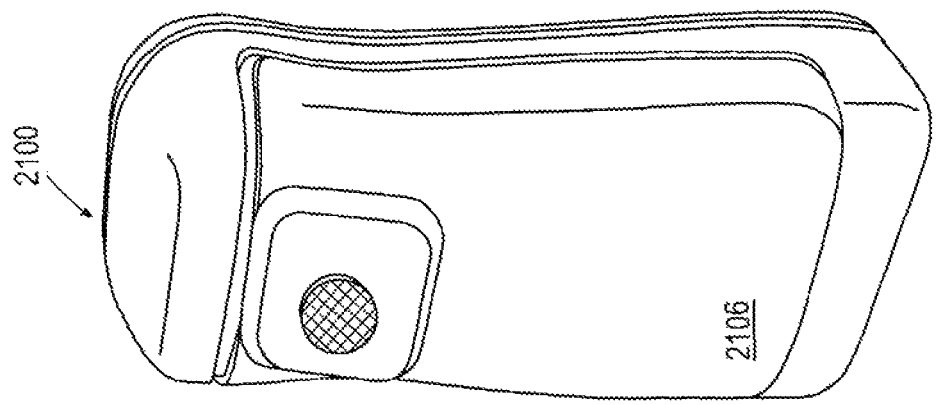
FIG. 13D shows a perspective view of the rear of an ejector device shown in FIG. 13A.
Figure 13C:
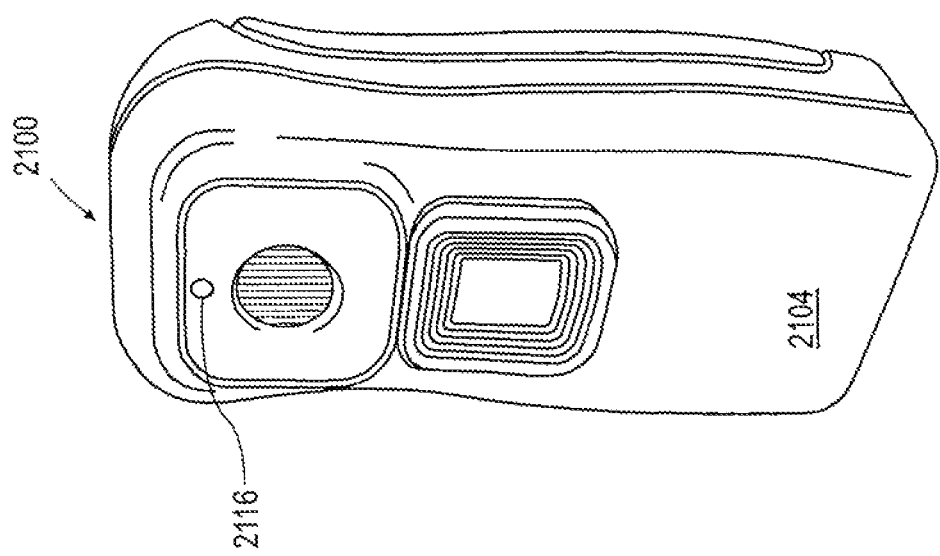
FIG. 13C shows a perspective view of FIG. 13A.
Figure 13E:
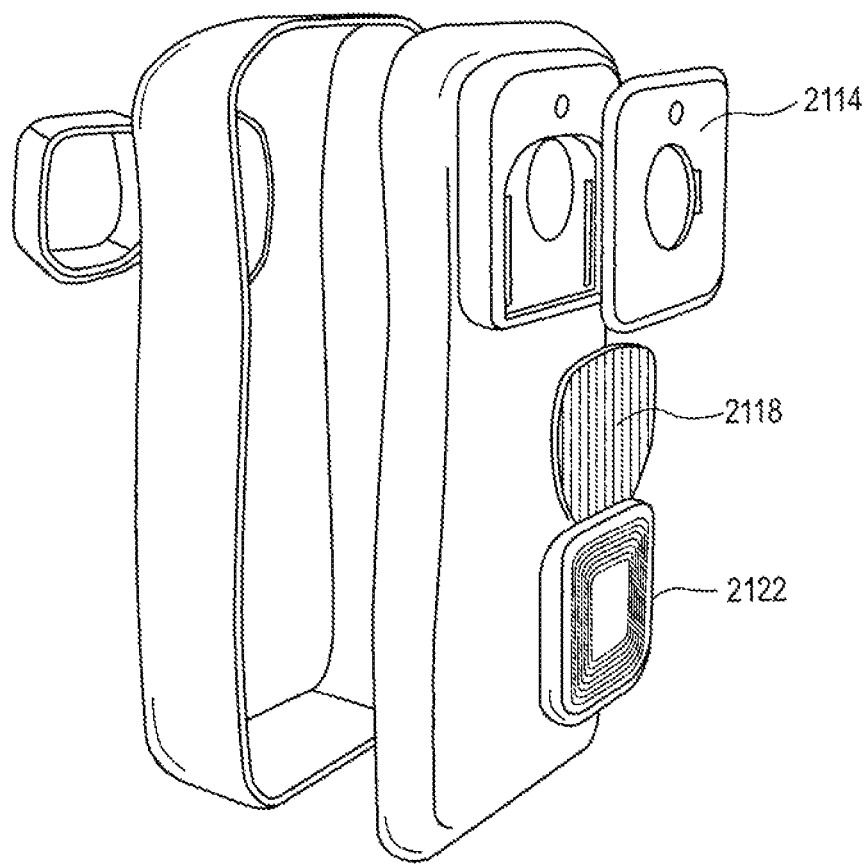
FIG. 13E shows an exploded perspective view of parts of a housing of an ejector device of FIG. 13A, in one implementation.

FIGS. 13A-D show another implementation of ejector device. The housing 2100 formed by components molded from plastic or other suitable material is generally defined by a front portion 2104 and a rear portion 2106. The front portion 2104 includes a fluid delivery area 2108 and an activation mechanism 2110. The fluid delivery area 2108 further defines a delivery aperture 2112 formed through a cover bezel 2114 and through the housing. The fluid delivery area 2108 also includes a multifunction LED 2116. The activation trigger 2110 includes an aperture cover plate 2118 and a thumb rest 2120. One or more raised edges 2122 may be formed around the perimeter of the thumb rest 2120 to assist with positioning the thumb of a user on the activation trigger 2110. In the implementation shown, the cover plate 2118 and thumb rest 2120 may be formed integrally in one piece or in multiple parts. The cover plate 2118 fits within a slot formed by the front portion 2104 and the cover bezel 2114 (FIG. 13E) and is operable to slide up and down within the slot thereby allowing the cover plate 2118 to seal the delivery aperture 2112 and protect the ejector assembly behind the aperture and internal components from external debris and contamination. Optionally, a back surface of the cover plate 2118 may be coated with material containing silver particles to prevent bacteria from forming in and around the inside of the delivery area.

Figure 13F:
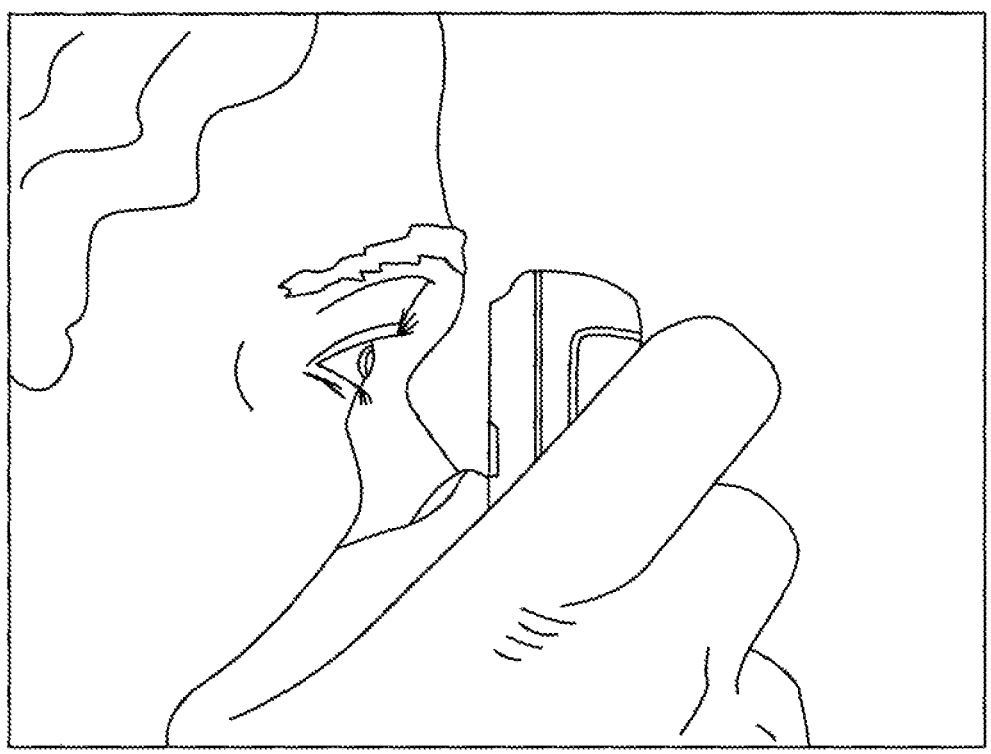
FIG. 13F shows a diagram depicting an ejector device aligned with the eye of a user.

FIG. 13F is a schematic diagram depicting a user aligning the device in the direction of their eye prior to delivering a dose of ophthalmic fluid droplets. The ergonomic design of the device allows the user to place their thumb on the thumb rest located on the device and promotes the thumb to take on a slightly bent position. The proximal phalanx of the thumb may then be placed against the user's cheek bone for steadying the device while the user aligns the delivery aperture with their eye. A multifunction LED, including, optionally, a back-lit polished ejector plate, may also aid in alignment. When the user's thumb is placed against their cheek bone, the delivery aperture can be easily aligned at the optimal distance of 2-3 cm from the eye's surface. The user may then locate their index finger on the delivery button, and when ready may depress the delivery button for delivering ophthalmic fluid to the surface of their eye.

Thus, the combination of the position of the thumb rest and the placement of the back of the thumb on the cheek bone provide a natural and repeatable alignment feature and process. Depending on the user's anatomy, a different portion of the thumb or hand may be aligned with an alternate location on the face to affect proper alignment. Alternatively, the device can be held a suitable distance during use, for example, as noted with respect to distance d shown in FIG. 1A. The suitable distance may vary with the type of subject and application. For example, for veterinary subjects, the device may be held a longer distance than for a human subject. Additionally, the device may be held in the palm of the hand and aligned without using the hand or its digits and instead with a spacer or aided by an alignment device as described above. Alternatively, any portion of the hand or its digits can be used to hold the device and any portion of the hand or its digits may be used to activate the delivery button. By way of example, the device can be held in the hand with the pinky spacing the device from the face and the thumb depressing a delivery button located on the side of the device housing.

During use, the device is held, turned on, aligned, and the delivery button depressed. Turning on the device may manually occur by activation of a physical activation trigger or may occur automatically or in response to a condition, e.g. removal of the device from a docking station. The device may cycle through a cleaning cycle once activated. The properly aligned housing delivers the fluid in the form of the droplet stream to the target.

In some instances, it may be desirable to control the temperature of the fluid in the device outside of the ejection cycle. In these implementations, the device may include a cooler, e.g., a Peltier device, for keeping the fluid cool where needed. The device may also include a heater for warming the fluid to a predefined temperature, e.g., the eye surface temperature of the person to whom the fluid is to be administered. The temperature range may be controlled by the controller.

Figure 14A:
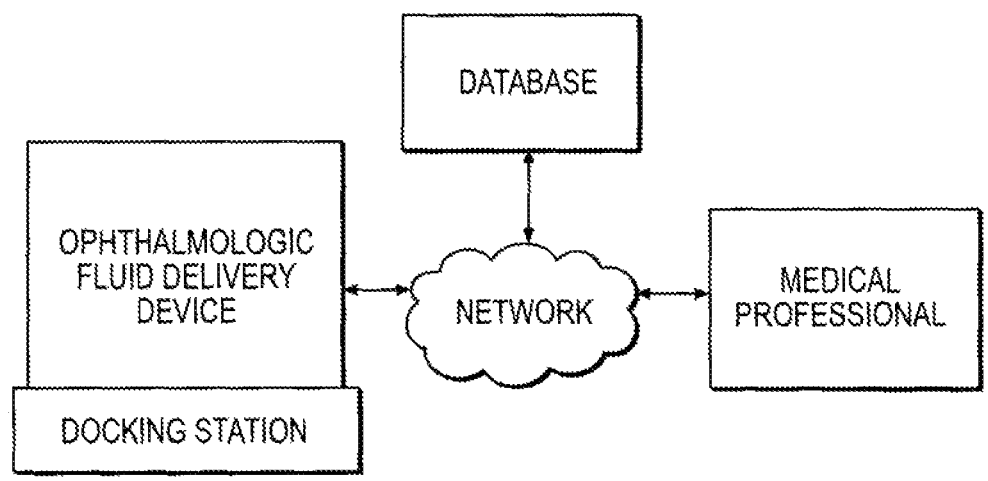
FIG. 14A shows an implementation of a communications system.
Figure 14B:
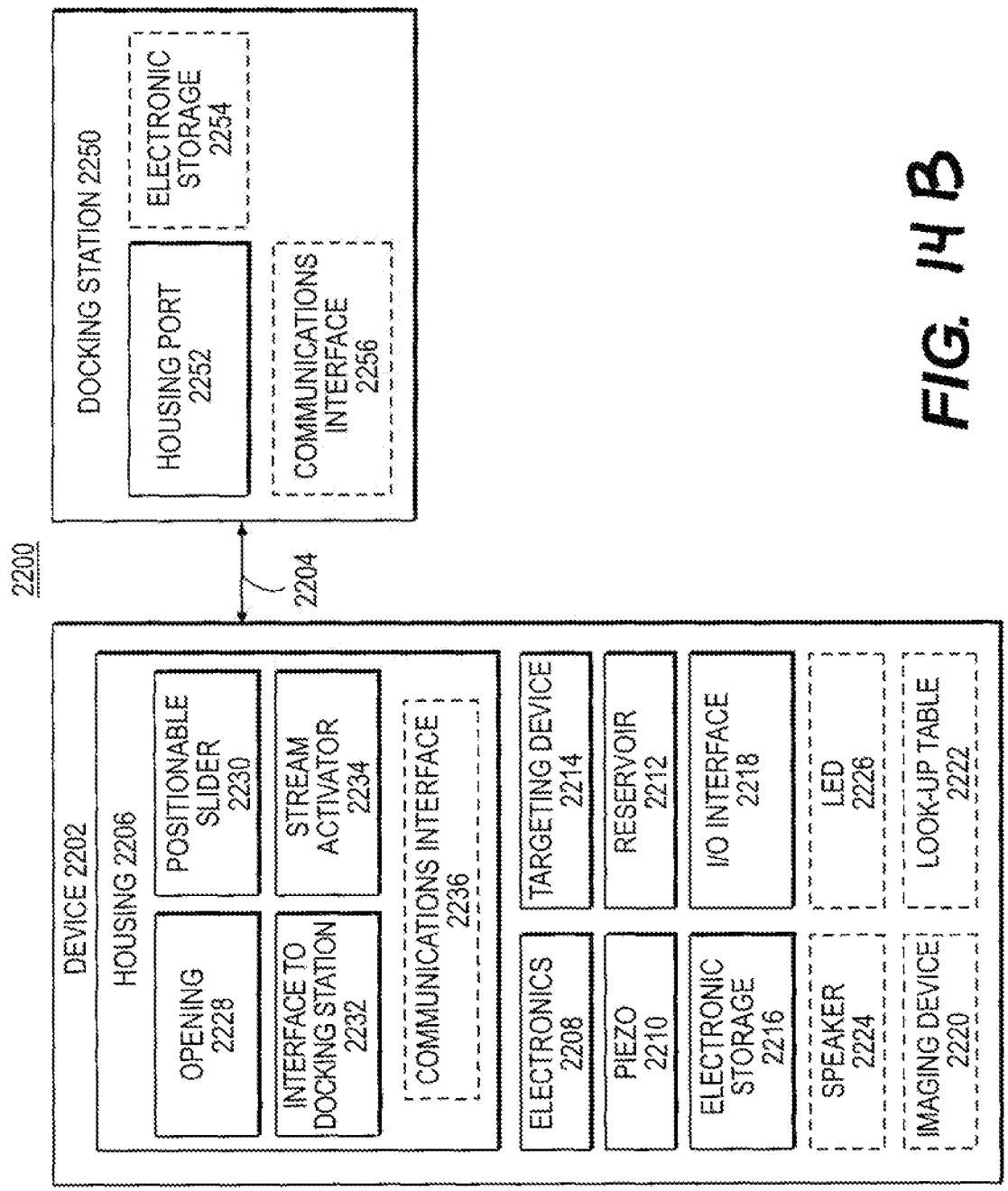
FIG. 14B shows a block diagram depicting an ejector device and a docking station in communication.

FIG. 14A shows a communication system that includes the ejector device. The device may be used in combination with a docking station. Details of this system and a docking station are more fully disclosed in U.S. patent application Ser. No. 13/184,468, filed Jul. 15, 2011, and incorporated herein by reference. FIG. 14B shows a block diagram showing a device 2202 and a docking station 2250 in communication. The device 2202 may include a housing 2206, electronics 2208, an ejector mechanism, e.g., piezo 2210, a reservoir 2212, a targeting device 2214, an electronic storage 2216, and an input/output (I/O) interface 2218. The device 2202 also may include an imaging device 2220, a lookup table 2222, a speaker 2224, and an LED 2226.

The housing 2206 may be made from, for example, injection molded plastic or any other suitable, durable, or lightweight material. The housing 2206 may include an opening 2228, a positionable slider 2230, an interface 2232 that sends communications to and receives communicates from the docking station 2250, a stream activator 2234, and a communications interface 2236. The communications interface 2236 sends data to and receives data from a source external to the housing 2206 (see U.S. patent application Ser. No. 13/184,468, filed Jul. 15, 2011, and incorporated herein by reference) of the device 2202, and the docking station 2250. For example, the communications interface 2236 may be in communication with the database or with an I/O device, such as a keyboard.

The opening 2228 may be in the form of an aperture formed through an exterior surface of the housing 2206, and the opening 2228 allows fluid stored in the reservoir 2212 to exit the housing 2206. The opening 2228 may be similar to those explained earlier. The positionable slider 2230 may be similar to the thumb slider described earlier. The housing 2206 also includes an interface 2232 configured to receive a connection 2204. The connection 2204 may be, for example, a one-wire, two-wire, or I2C interface. The interface 2232 allows the device 2202 to send data to and receive data from the docking station 2250 over the connection 2204.

The housing 2206 also includes a stream activator 2234. The activator may be, for example, a button that protrudes from the exterior surface of the housing 2206, a switch, or any other tactile interface that is accessible to a user of the device, such as the switches described above. The activator 2234 may be on a side of the housing 2206 that is opposite from the side of the housing 2206 that includes the opening 2228 and the slider 2230.

The housing 2206 also may include a communications interface 2236 that is in communication with the electronic storage 2216 and allows retrieval of data stored in the electronic storage 2216 and writing of data to the electronic storage 2216. The interface 2236 may be, for example, a universal serial bus (USB) connection, a serial connection, an Ethernet connection, or any other connection that allows reading and writing of data. Further discussion of these aspects appears in U.S. patent application Ser. No. 13/184,468, filed Jul. 15, 2011, and incorporated herein by reference.

The device 2202 includes the electronics 2208, which provide one or more output driver signals to the ejector mechanism actuator or piezo 2210. The piezo 2210 vibrates, moves, or distorts the ejector plate, and thereby the generator plate, in response to application of the output signals. The ejector plate and generator plate are in contact with fluid stored in the reservoir 2212, and, when the piezo 2210 distorts, fluid from the reservoir 2212 is ejected through one or more openings formed in the generator plate. In certain implementations, the motion of the ejector plate and thereby the generator plate, and in general, the operation of the ejector mechanism, causes a directed stream of droplets to exit the housing 2206 through the opening 2228.

As discussed in greater detail with regard to figures disclosing electronics, the electronics 2208 determine the frequency, voltage, duty cycle, and duration of the output driver signal 2342 that is applied to the piezo 2210. Additionally, the electronics 2208 are programmable such that the characteristics or properties of the output driver signals applied to the piezo 2210 may be adjusted to accommodate changes in the fluid and/or a dosage plan.

Figure 14C:
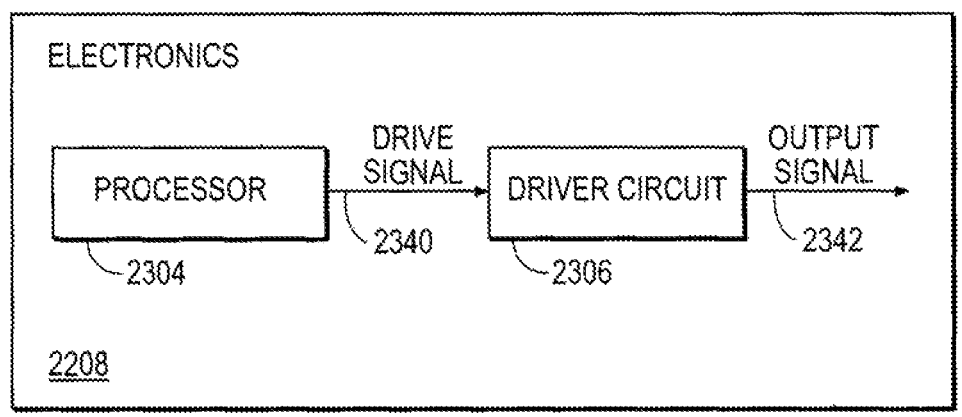
FIG. 14C shows a block diagram of a processor and a driver circuit.

FIG. 14C includes a processor 2304 and a driver circuit 2306. The processor 2304 provides an excitation signal 2340 to the driver circuit 2306, and the driver circuit 2306 generates an output driver signal 2342 that is applied to the piezo 2210. The properties of the output driver signal 2342 are determined from the properties of the excitation signal 2340. As discussed below, the output driver signal 2342 may include, for example, two or four separate output driver signals.

In one implementation, the piezo 2210 may be mounted on a printed circuit board (PCB) and contact a conductive surface on the PCB board (not shown). The conductive surface may be stainless steel. In some implementations, a conductive path may be formed via discrete wiring, not integrated with the PCB board that connects the piezo 2210 to an output of the driver circuit 2306. In some implementations, the conductive path may be a trace made directly on the PCB board. In these implementations, a conductive material may be placed between the piezo 2210 and the O-ring and reservoir 2212. The conductive material may be, for example an elastomer or "Zebra strip." In these implementations, the discrete wire may be eliminated and the output driver signal 2342 from the driver circuit 2306 may be provided to the piezo 2210 by a conductive trace formed directly on the PCB board.

In some implementations, the device 2202 may include a second piezo (not shown) that may be coupled to the reservoir 2212. In this implementation, the driver circuit 2306 may be configured to generate four output driver signals 2342 to drive the two separate piezos. By way of example, the second piezo may be mounted directly to the surface of the reservoir 2212 such that the reservoir 2212 vibrates with the second piezo. This vibration may help to ensure that the fluid in the reservoir 2212 remains in a fluid state, to help prevent the formation of crystals or other solid particles in the reservoir 2212, to maintain homogenous mixture, etc. In the case of medications provided as a suspension, the vibration may be operable to mix the medication prior to use.

The reservoir 2212 may be pre-filled with fluid when the device 2202 is manufactured. The device 2202 may be programmed at the time of manufacture of the device 2202. Alternative reservoirs as discussed can be used without limitation. The device 2202 may also include the targeting device 2214. The targeting device 2214 may assist the user to align the device 2202 with an eye of the subject. The targeting device 2214 may be, for example, an LED that shines in the subject's eye, a reflective or shiny surface that reflects the subject's eye, and/or a CCD camera that images the subject's eye and provides a signal to the electronics 2208. By way of example, the targeting device 2204 may include a reflector to provide the user with an image of his or her eye when the device 2202 is correctly positioned, or may include a light source, such as a low intensity LED, for shining into the user's eye when the device 2202 is correctly positioned. The targeting device 2214 may include a sensor that determines whether or not the subject's eye is open. The targeting device 2214 may include an element that shows a reflection of the subject's eye when the device 2202 is properly aligned with the eye. For example, the ejector plate, generator plate, and/or piezo 2210 may be made from a reflective material that shows a reflection of the subject's eye when the opening 2228 and the piezo 2210 are aligned with the subject's eye. This type of targeting device is helpful for instances where the subject is using the device 2202 to administer a directed stream of droplets to their own eye.

The targeting device 2214, e.g., LED, may receive power from a power module (not shown), and a signal to turn ON or OFF from the processor 2304. The processor 2304 also may provide a signal to the speaker 2224 to turn ON or OFF. In certain implementations, the power module may be one or more batteries.

In alternative implementations, all or part of the surface of the ejector mechanism or the housing adjacent thereto may be coated with a reflective layer. A coating layer may be both protective and reflective. Alternatively, the surface may have been formed to be reflective. For example, the surface may be made of stainless, nickel-cobalt, or other reflective material. A surface may have been formed or polished to be reflective. In addition to making the surface reflective, the surface may also be backlit on its surface or around its perimeter. In ophthalmic applications, a reflective surface aids the user in aligning the ejector assembly with the eye.

The device 2202 also includes the electronic storage 2216 and the I/O interface 2218. In addition to storing data such as images of the subject's eye, the electronic storage 2216 stores instructions, perhaps as a computer program, that, when executed, cause a processor included in the electronics 2208 to communicate with other components in the device 2202. The processor may be, for example, a state machine such as an FPGA or an ASIC. The excitation signal 2340 may be generated by a signal generator. Information on the electronic storage 2216 may be accessed through the interface 2218 or the interface 2236 (which communicates with a database), and access to the contents of the electronic storage is controlled, e.g., password restricted to allow certain activities to be conducted by certain medical personnel, e.g., doctors or pharmacists wishing to adjust dosages. Insofar as the computer is Internet enabled, information may be uploaded via the Internet, e.g. to a server for access by medical personnel to allow progress and proper subject use to be monitored and allow dosages to be adjusted over the Internet, e.g., by uploading revised dosage information to a server by the medical personnel and then pushing to the device via the Internet or downloading by the user. The device itself may be Internet enabled to allow usage information and image information to be uploaded in real time and new information to be downloaded to the device in real time. Insofar as the device is Internet enabled it may be provided with a user interface, e.g. screen and keyboard or touch sensitive screen.

The input/output interface 2218 provides an interface that allows data and/or commands to be input to the device 2202 and/or read from the device 2202. The input/output interface 2218 may receive data from a device such as a keyboard, a mouse, a communications port, an electronic processor executing on a device separate from the device 2202, or a display. The input/output interface 2218 also may include software that allows communication between the device 2202, the components of the device 2202, and/or an external device. The interface 2218 may provide the user with access to the device 2202 when the device 2202 is plugged into a computer, such as a laptop or palmtop or cellular phone with screen and user input capabilities, through the interface 2218.

The device 2202 also may include an imaging device 2220. The imaging device 2220 may be a charged coupled device (CCD) that is aligned with the opening 2228 such that the imaging device 2220 captures an image of the subject's eye through the same aperture that delivers the directed stream of droplets of fluid. In some implementations, the imaging device 2220 is mounted on an external surface of the housing 2206 in a location other than the location of the opening 2228. Images collected by the imaging device 2220 may be transferred from the device 2202 through the I/O interface 2218, the communications interfaces 2236 or 2256, and/or the images may be stored in the electronic storage 2216. The images may be uploaded to the database and stored in association with the subject's medical records, as more fully explained in U.S. patent application Ser. No. 13/184,468, filed Jul. 15, 2011, and incorporated herein by reference.

The imaging device 2220 and the electronics 2208 may be operable to control the capture of images during or at selectable times before or after ejection of fluid from the device 2202. In some implementations, the capture of images may be triggered by the user by, for example, depressing a button or the stream activator 2234. For example, saline droplets may be directed from the device 2202 towards the eye to exert a pressure on the cornea and images may be taken to determine the effect. The images may be saved as discussed herein.

The device 2202 also may include the look-up table 2222. The look-up table 2222 may be stored on the device 2202, for example, in the electronic storage 2216, or the look-up table may be stored separately from the device 2202, for example, in the database. The look-up table 2222 includes information specific to fluids that may be used in the device 2202. For example, because viscosities of fluid drugs vary, depending on the fluid in the reservoir, the piezo 2210 may require application of output driver signals having a frequency tailored to the fluid in the reservoir. This medication-specific variation may be accounted for by varying the properties, such as the frequency, voltage, and/or duration of the output driver signals produced by the electronics 2208 and applied to the piezo 2210. The look-up table 2222 may include information specific to the medication that is retrieved and used by the electronics 2208 to set the output driver signals.

The look-up table 2222 also may include medication-specific information that relates to the subject's treatment plan. For example, the look-up table may include information specifying that a first medication is to be applied three times a day, while a second medication is to be applied once a day. This treatment plan information is used by the electronics 2208 to determine, for example, when to trigger a reminder alert for the subject based on the type of medication that is placed in the reservoir.

In some implementations, the look-up table 2222 on a specific device 2202 may be edited by a professional, e.g., medical professional to account for changes in the subject's condition. The interface 2236 may be operable to download information, for example, via an external I/O device or directly from the database, perhaps via the Internet. The downloaded information may include one or more of revised dose amounts, revised dose times, and medication type to be dispensed. The device 2202 may be configured such that the electronics 2208 controls the dispensing of medication in response to pre-defined information or the downloaded information.

The device 2202 also may include a speaker 2224 and an illuminator 2226, both of which may be used, in conjunction with the electronics 2208, to provide a perceivable alert to the user of the device 2202. The device 2202 may provide other perceivable alerts. For example, the device 2202 may vibrate to attract the user's attention. The device 2202 may produce an audible alarm or enunciator, or visual indicator controllable by the electronics 2208 to provide feedback to the user, for example, visual or audible feedback to indicate when a full dose has been reached. The illuminator 2226 may be an LED or other device that emits visible radiation in response to electrical input.

In some implementations, the illuminator 2226 may include multiple light sources of different frequencies for illuminating the eye, or may include a variable frequency light source, such as light of different colors and frequencies (e.g., red, blue, green, white, infrared (IR), ultraviolet (UV)). The device may include a cobalt blue light (generated, for example, by using a filter) for use with fluorescein to illuminate the cornea for identifying corneal ulcers and scratches. The illuminator 2226 may be a radiation source that emits frequencies above 280 nm wavelengths for illuminating the eye. The illuminator 2226 may be operable to pulse the light for different periods of time, for example, 20 ns to limit pupil reaction and permit analysis of the eye with different frequency optical detectors, scanners or cameras. The illuminator 2226 may include an adaptive optics chip to perform wavefront correction for clearer images, for example, a MEMS based adaptive optics chip. The device may also include a fixation source e.g., an LED or LED pattern to define a moving eye-focusing image and assist with pediatric usage. This also serves to move or rotate the eyeball during application of medication to assist in spreading the medication across the corneal surface.

The docking station 2250 includes a housing port 2252 (including, without limitation, a docking station) that is configured to receive the device 2202. The housing port 2252 may be recessed such that, when the device 2202 is received by the docking station 2250, the device 2202 is seated securely and is stably held by the docking station 2250. Alternatively, the docking station may wirelessly couple to the device 2202. The docking station 2250 also may include a communications interface 2256 that reads and writes data from the docking station 2250 and/or the device 2202. The communications interface 2256 may be, for example, a USB connection, an Ethernet connection, or a serial connection. The docking station 2250 also may include a memory or an electronic storage 2254.

The electronic storage components 2216 and 2254 may be volatile memory, such as RAM. In some implementations, the electronic storage components 2216 and 2254 may include both non-volatile and volatile portions or components.

Many implementations of the invention have been disclosed. This disclosure contemplates combining any of the features of one implementation with the features of one or more of the other implementations. For example, any of the ejector mechanisms or reservoirs can be used in combination with any of the disclosed housings or housing features, e.g., covers, supports, rests, lights, seals and gaskets, fill mechanisms, or alignment mechanisms. Further variations on any of the elements of any of the inventions within the scope of ordinary skill is contemplated by this disclosure. Such variations include selection of materials, coatings, or methods of manufacturing. Any of the electrical and electronic technology can be used with any of the implementations without limitation. Furthermore, any networking, remote access, subject monitoring, e-health, data storage, data mining, or internet functionality is applicable to any and all of the implementations and can be practiced therewith. Further still, additional diagnostic functions, such as performance of tests or measurements of physiological parameters may be incorporated into the functionality of any of the implementations. Performance of glaucoma or other ocular tests can be performed by the devices as a part of their diagnostic functionality. Other methods of fabrication known in the art and not explicitly listed here can be used to fabricate, test, repair, or maintain the device. Furthermore, the device may include more sophisticated imaging or alignment mechanisms. For example, the device or base may be equipped with or coupled to an iris or retina scanner to create a unique identification to match a device to the user, and to delineate between eyes. Alternatively, the device or base may be coupled to or include sophisticated imaging devices for any suitable type of photography or radiology.

To assist in understanding the present invention, the following Example is included. The experiments described herein should not, of course, be construed as specifically limiting the invention and such variations of the invention, now known or later developed, which would be within the purview of one skilled in the art are considered to fall within the scope of the invention as described herein and hereinafter claimed.

EXAMPLES

Example A: Modes of Operation

Although many arrangements are possible, one implementation uses a piezoelectric-driven ejector mechanism which includes a 6 mm diameter, 160 μm thick Ni—Co generator plate that is bonded to a 20 mm, 50 μm thick 304 stainless steel ejector plate annulus. The ejector plate annulus includes a 4 mm diameter central opening which is aligned with the generator plate, and the piezoelectric actuator is attached directly to the ejector plate. A modulation frequency of 108.0 kHz is applied to the piezoelectric actuator, causing the ejector plate to oscillate at approximately the same frequency. Digital holographic microscopy images are captured to observe oscillation of the generator plate.

Figure 15A:
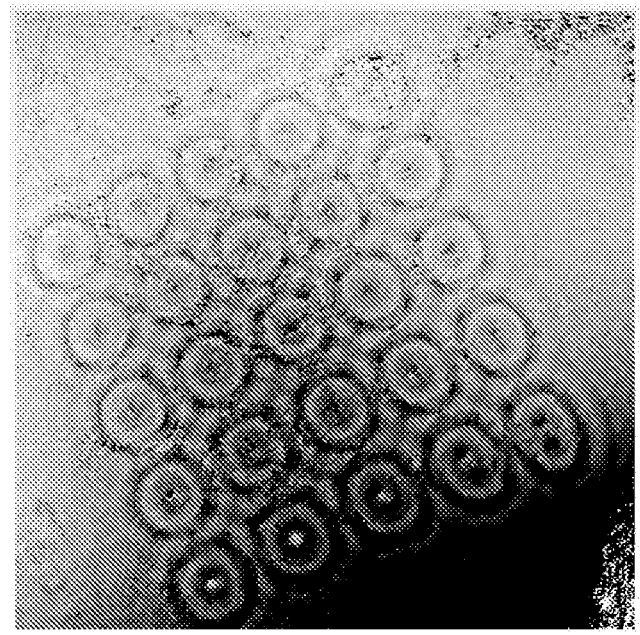
FIGS. 15A-15B illustrate an active region of an implementation of a generator plate, and a digital holographic microscopy image of oscillation of the generator plate.
Figure 15B:
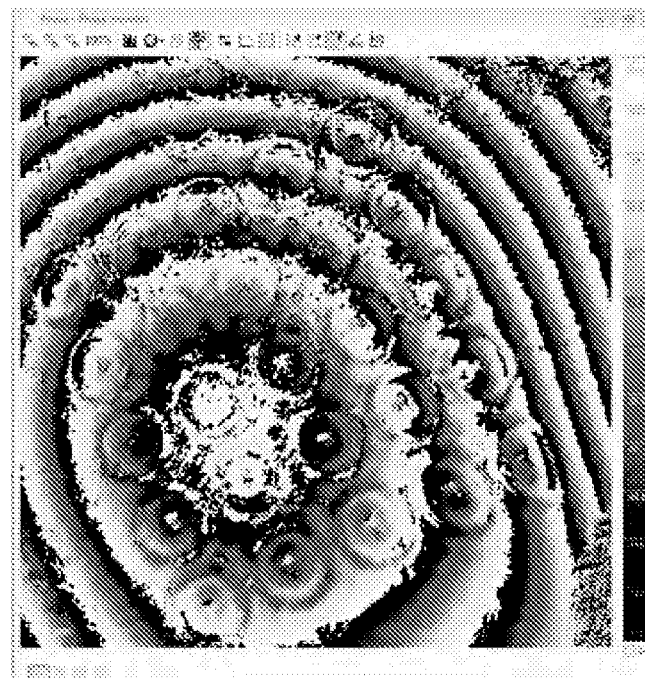
Figure 16:
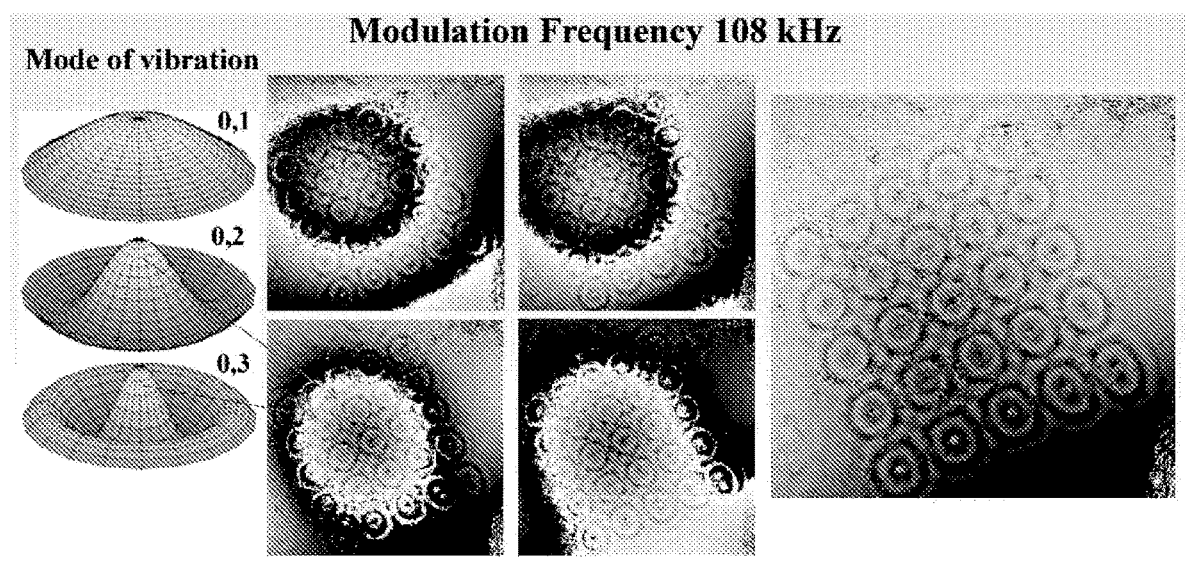
FIG. 16 illustrates modes of operation of an active region of an implementation of a generator plate, and digital holographic microscopy image of oscillation of the generator plate.

Simulation of normal mode of oscillation is obtained, and 0,2 and 0,3 is experimentally observed for the ejector plate/generator plate configuration. See, e.g., FIGS. 15A-B, which illustrate the active region of the generator plate including an array of openings (FIG. 15A) and a digital holographic microscopy image of the oscillation of the active region of the generator at a modulation frequency of 108 kHz (FIG. 15B). FIG. 16 illustrates digital holographic microscopic images of the active region of the generator plate showing areas of various observed modes of oscillation. This mode is associated with a maximum amplitude and displacement of the central, active region of the generator plate.

Example B: Effect of Piezoelectric Actuator Mounting Configurations

Figure 17A:
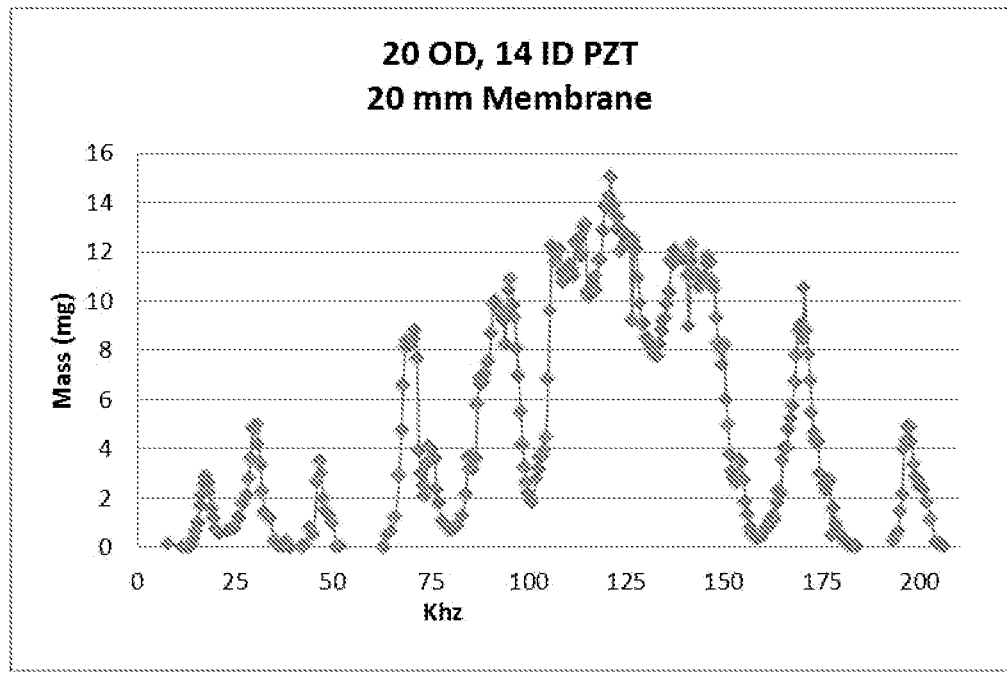
FIG. 17A-17C illustrate spray performance of implementations of an ejector mechanism.
Figure 17B:
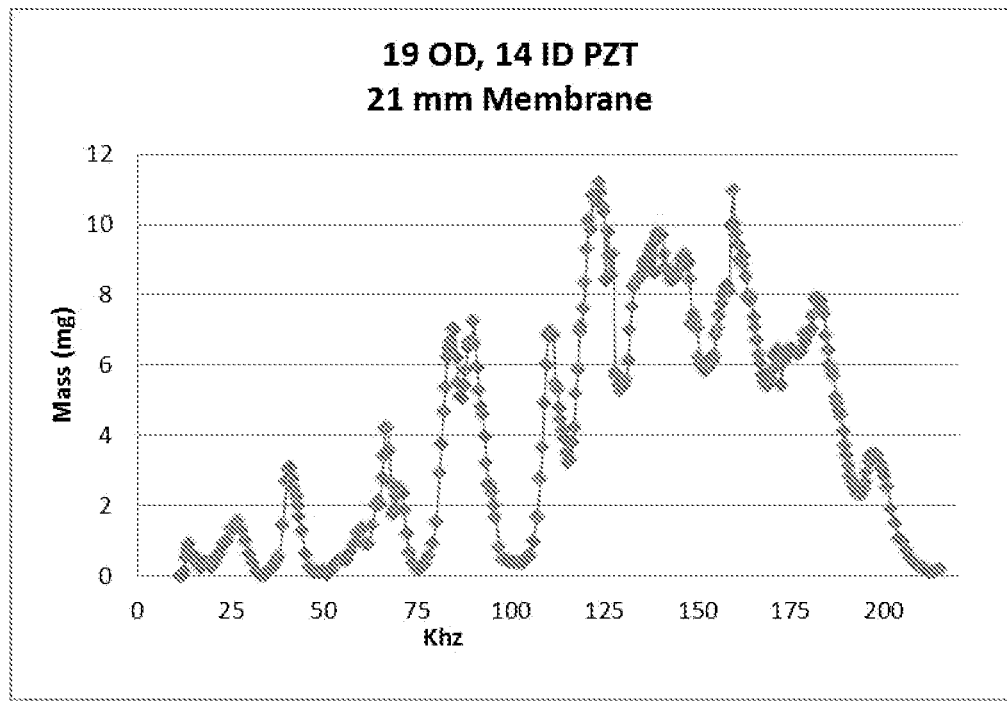
Figure 17C:
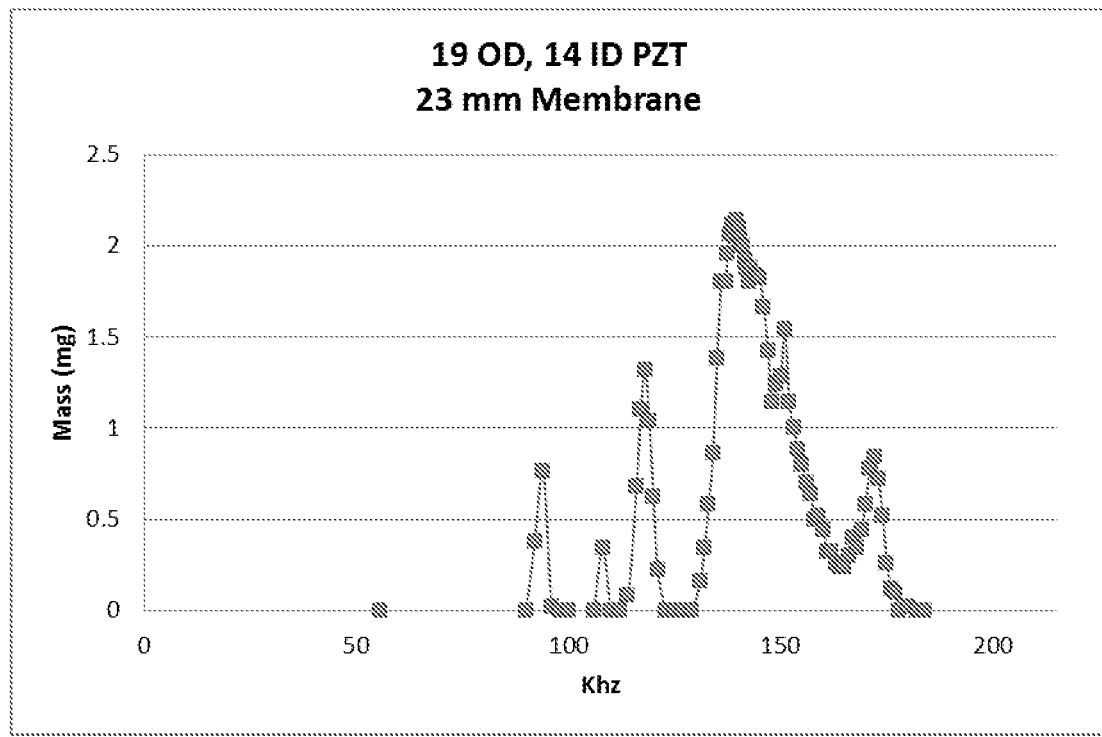

In certain implementations of ejector mechanisms of the disclosure, spray performance may be impacted by mounting configurations of the piezoelectric actuator. For instance, FIGS. 17A-17C show spray performance as piezoelectric mounting is progressively shifted away from the edge of the ejector plate (membrane), starting with A) edge mount, B) 1 mm from the ejector plate edge, and C) 2 mm from the ejector plate edge. Modes and ejection performance is increasingly suppressed as the piezoelectric is moved toward the interior of the ejector plate and closer to the generator plate.

Figure 18:
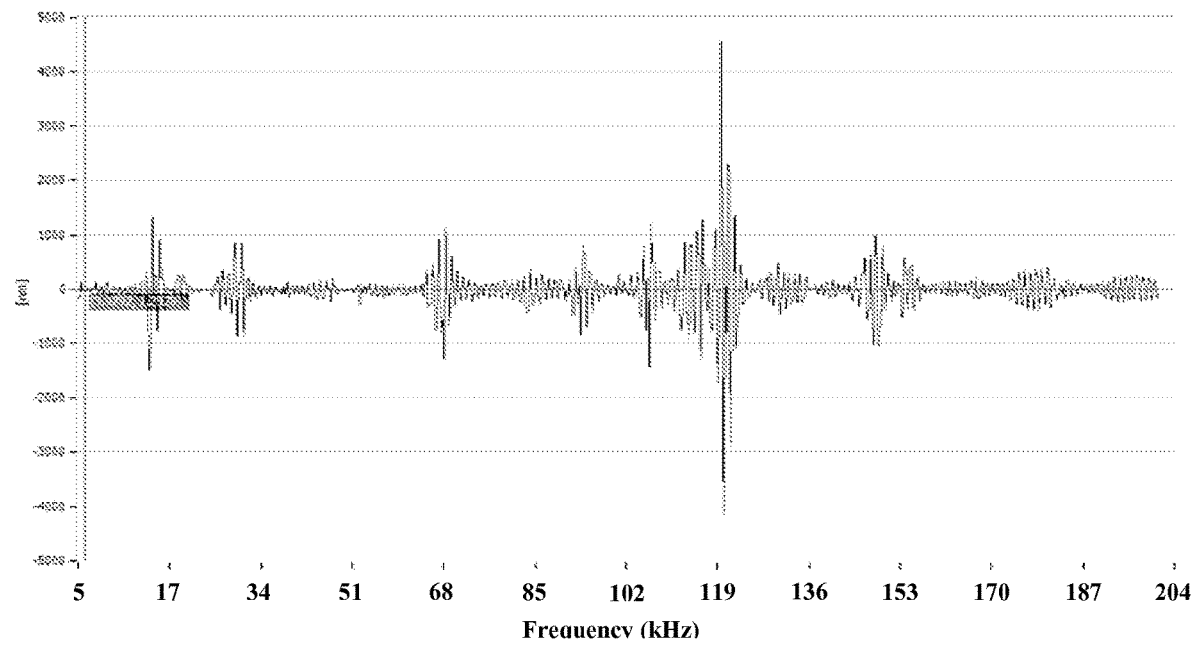
FIG. 18 illustrates a frequency sweep vs. displacement of an exemplary ejector mechanism of the disclosure.
Figure 19:
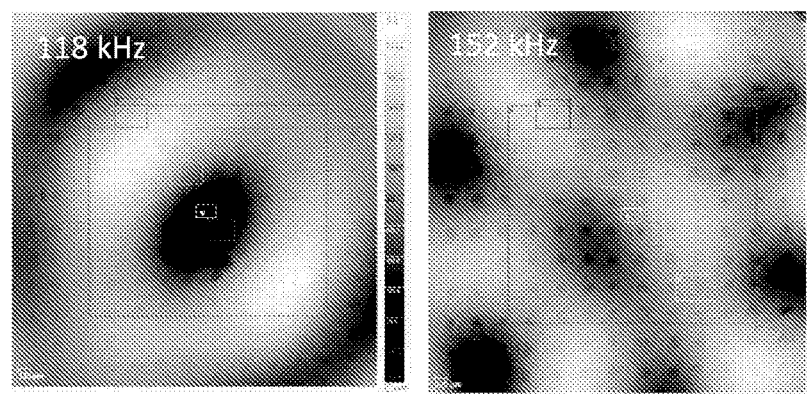
FIG. 19 illustrates digital holographic images of measured generator plate eigenmodes of an exemplary ejector mechanism of the disclosure.
Figure 22:
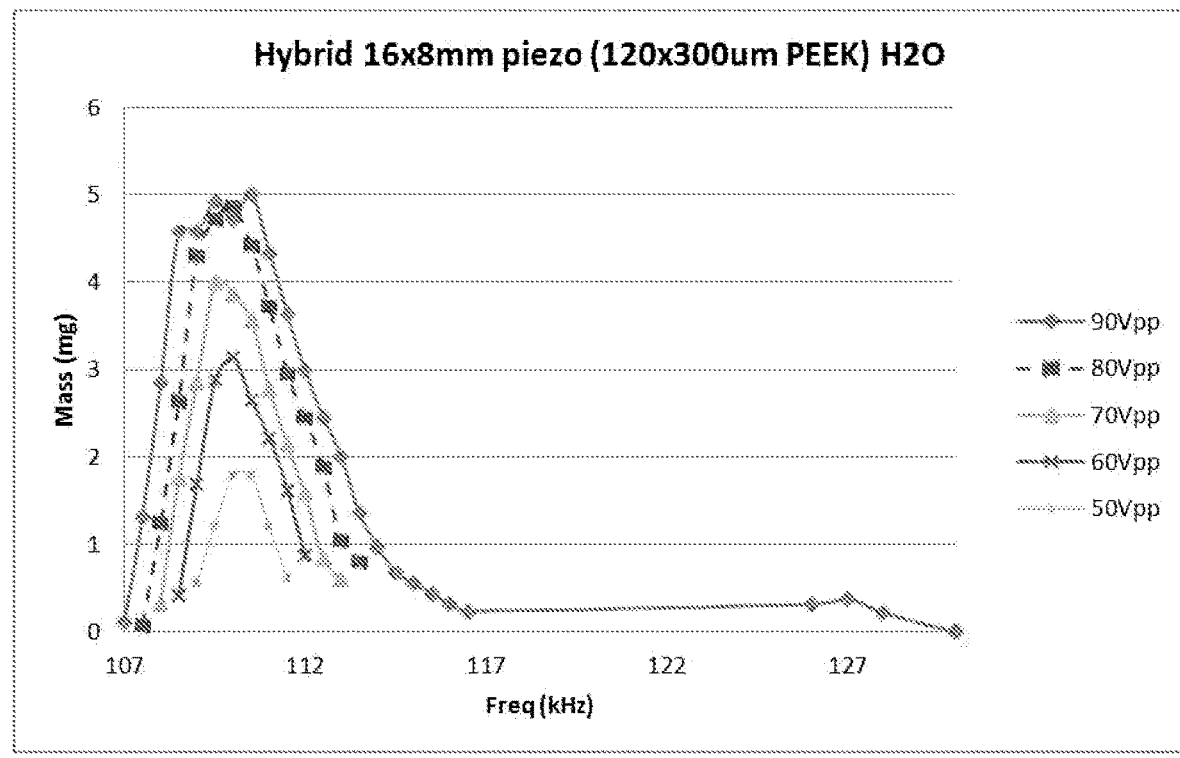
FIG. 22 illustrates a frequency sweep vs. ejected mass for a range of applied drive voltages of an exemplary ejector mechanism of the disclosure.
Figure 23:
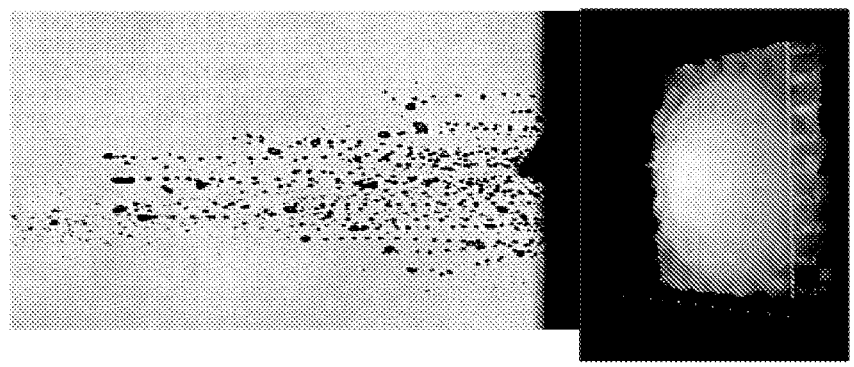
FIG. 23 illustrates a high speed image of a droplet spray overlaid with a digital holographic image of a normal mode of operation of exemplary ejector mechanisms of the disclosure.
Figure 24A:
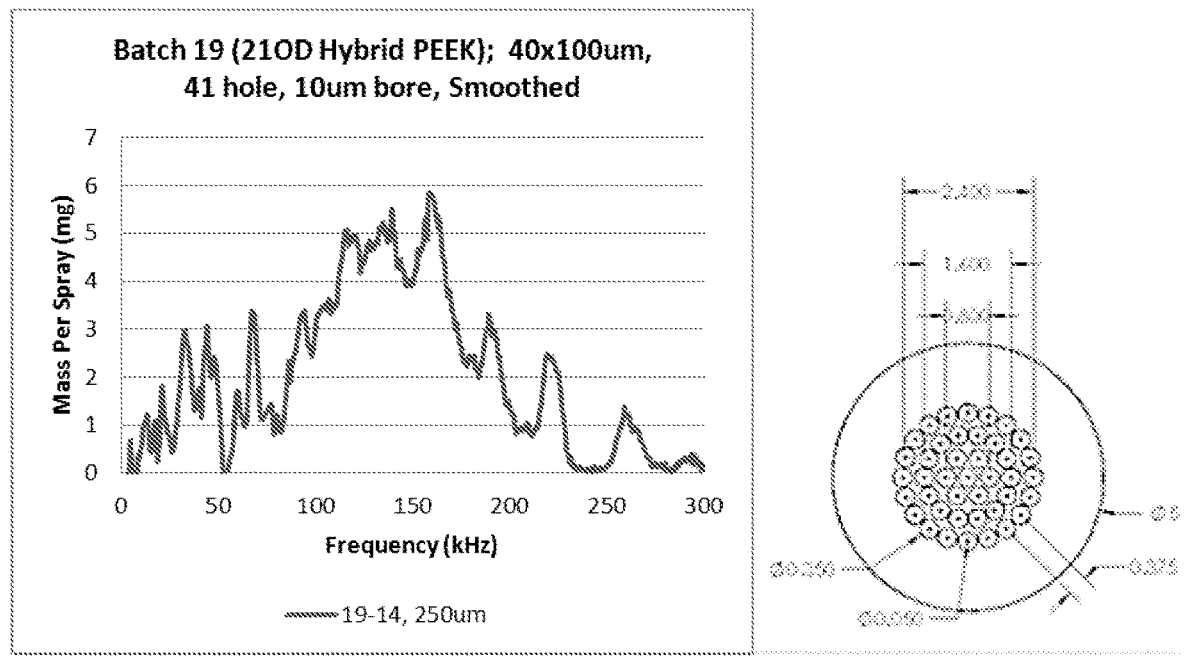
FIG. 24A-24B illustrates frequency sweeps vs. ejected mass for a range of generator plate opening configurations of exemplary ejector mechanisms of the disclosure.
Figure 24B:
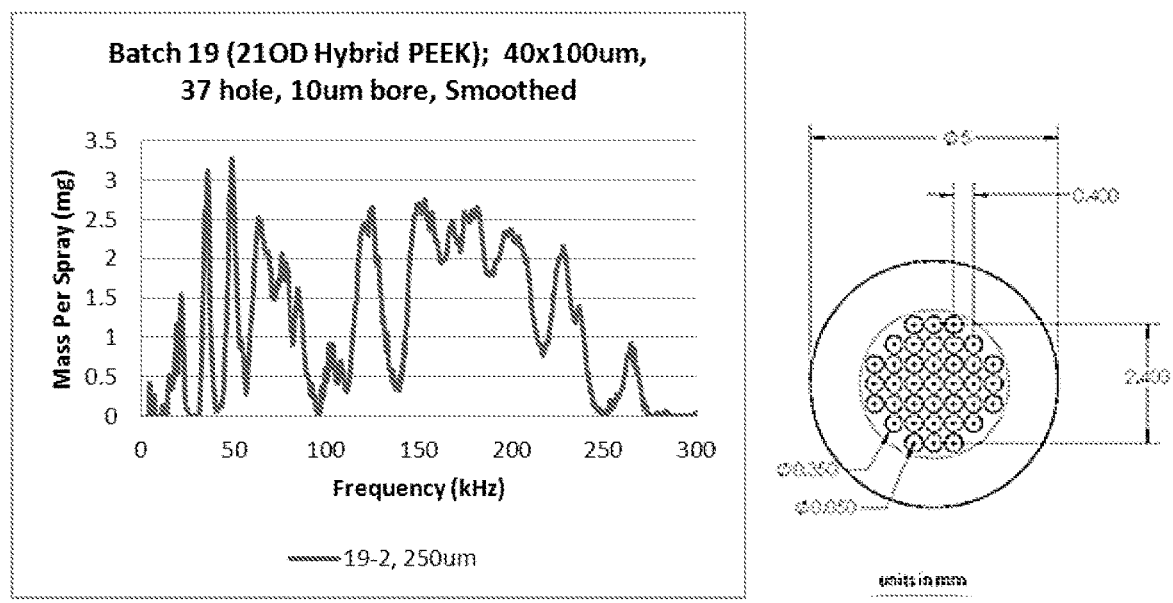
Figure 25:
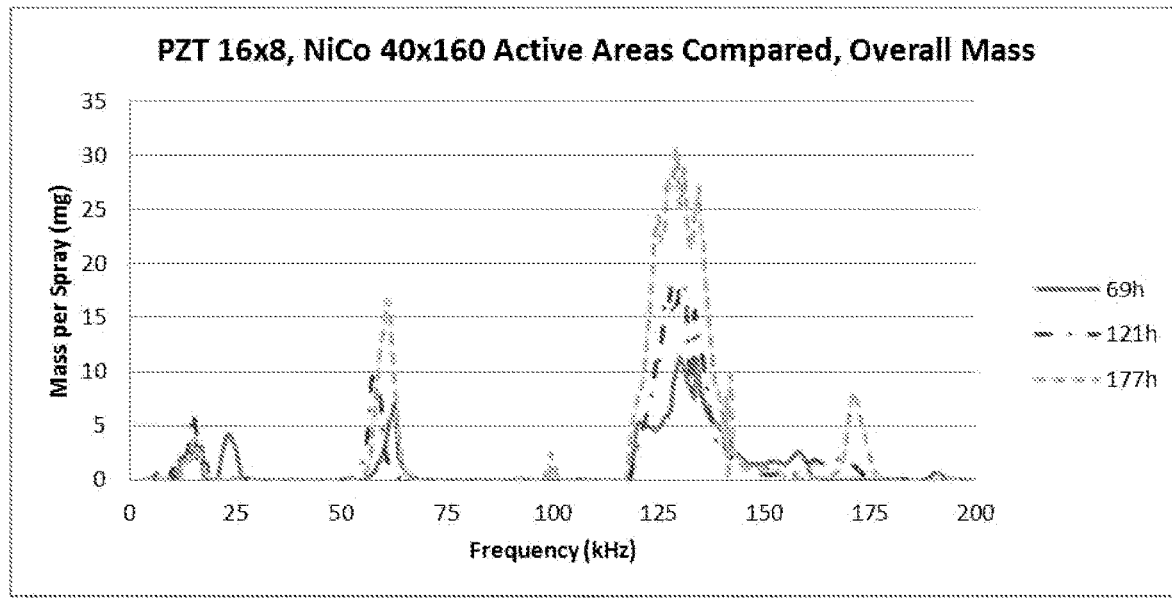
FIG. 25 illustrates a frequency sweep vs. ejected mass for a range of generator plate opening configurations of exemplary ejector mechanisms of the disclosure.
Figure 26:
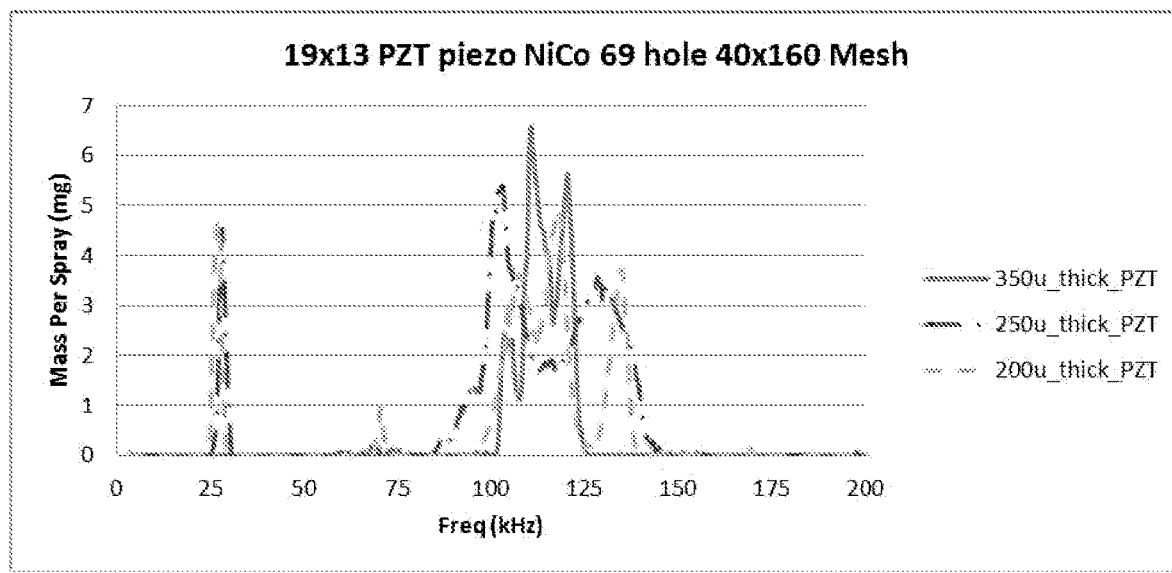
FIG. 26 illustrates a frequency sweep vs. ejected mass for a range of piezoelectric actuator thicknesses of exemplary ejector mechanisms of the disclosure.

FIG. 18 shows a frequency sweep (from 5 kHz to 200 kHz) vs. displacement of a piezoelectric actuated NiCo generator plate. This measure provides a means of directly recording the dynamic oscillation and identifying the resonance frequencies which produce the optimum amplitude of displacement, e.g., +/−4.5 microns at 118 kHz vs.+/−1 micron for 152 kHz. These frequencies are often associated with optimum mass ejection and droplet generation. Digital holographic imaging at select excitation frequencies is also often used to identify the generator plate's eigenmodes by direct imaging.

FIG. 19 shows measured generator plate eigenmodes using digital holographic imaging of 20 mm, OD, NiCo generator plate, and a piezoelectric actuator with a 20 mm, OD and 14 mm, ID, excited at resonance frequencies of 120 kHz and 152 kHz.

FIG. 20 shows an example of a NiCo generator plate excited at 118 kHz with a sine waveform at 90 Vpp. As shown in FIGS. 20A and 20B, the annular piezoelectric actuator driven at 118 kHz excites axisymmetric modes that can be viewed by digital holographic imaging (DHM). FIG. 20C shows simulated modes using FEM techniques. DHM, therefore provides a quick means of identifying optimum piezoelectric structures, optimum placement of the piezoelectric actuator on the ejector plate, and amplitude and velocity associated with each excitation voltage and frequency.

Example C: Effect of Fluid Loading

In certain implementations of ejector mechanisms of the disclosure, fluid loading may affect performance of an ejector mechanism. FIG. 21 (PZT 19 OD, 14 ID 0.225 mm thick; NiCo generator plate, 20 μm hole, 50 μm thick mounted on a post tab attachment configuration; 50 μm thick stainless steel ejector plate, 21 mm OD, 4 mm, ID) shows that increased piezoelectric drive voltage leads to a direct increase in displacement and oscillation of the generator plate in the +/−Z plane. Digital holographic imaging is used to measure the displayed dynamics of the generator plate oscillation while in contact with fluid.

FIG. 22 (PZT 16 OD, 8 ID) shows increased piezoelectric drive voltage leads to a direct increase in displacement and oscillation of the generator plate in the +/−Z plane. This oscillating plate, when in contact with fluid produces an oscillating pressure gradient which induces laminar flow through the openings in the ejector plate. FIG. 22 shows a direct correlation between generator plate displacement and spray performance.

Example D: Effect of Eigenmode

In certain implementations of ejector mechanisms of the disclosure, the eigenmode of the generator plate may affect the shape of the generator plate, and the resulting spray, during excitation. FIG. 23 shows a high speed image frame representative of an ejected spray from a ejector mechanism of the disclosure overlaid with digital holographic image captured from a similar ejector mechanism, which displays the normal mode of generator plate oscillation at 140 kHz.

Example E: Effect of Placement of Openings and Piezoelectric Actuator Thickness

In certain implementations of ejector mechanisms of the disclosure, the placement and configuration of openings of the generator plate may affect spray performance. FIG. 24A-B shows that placement and configuration of openings of the generator plate has an impact on spray performance. As shown in FIG. 24A, circular symmetric placement of openings leads to about a two-fold increase in spray volume (mass deposition) in comparison to a square hole array (FIG. 24B).

FIG. 25 (PZT 16 OD, 8 ID) shows spray performance is also increased by increasing the number of openings in a generator plate. Displayed is the mass deposition of distilled water sprayed from a generator plate having 69, 121 and 177 openings collected over a frequency scan from 4 to 200 kHz.

FIG. 26 (PZT 19 OD, 13 ID) shows that piezoelectric actuator thickness also affects spray performance. Displayed is mass deposition collected over a frequency scan from 4 to 200 kHz as a function of piezoelectric actuator thickness, for a generator plate have 69 openings.

Although the foregoing describes various embodiments by way of illustration and example, the skilled artisan will appreciate that various changes and modifications may be practiced within the spirit and scope of the present application.

What is claimed is:

1. An ejector device for delivering a fluid to a target, the device comprising:

a housing;

a reservoir disposed within the housing for receiving a volume of fluid; and an ejector mechanism in fluid communication with the reservoir and configured to eject a stream of droplets, the ejector mechanism comprising an ejector plate coupled to a separate generator plate, and a piezoelectric actuator coupled to the ejector plate;

the ejector plate having a first side and a second side opposite the first side, the second side of the ejector plate being coupled to the generator plate;

the generator plate having a first fluid intake side coupled to the second side of the ejector plate and in fluid communication with reservoir, and a second fluid exit side, the generator plate further including a plurality of openings formed through its thickness, the plurality of openings having an average opening diameter at the second fluid exit side of from about 20 μm to about 100 μm, which average opening diameter at the second fluid exit side is smaller than the average opening diameter at the first fluid intake side; and the piezoelectric actuator being coupled to one of the first side or the second side of the ejector plate, and being operable to oscillate the ejector plate, and thereby the generator plate, at a frequency and generate a directed stream of droplets;

wherein one or more of said plurality of openings are shaped so as to comprise a fluid entrance orifice, an entrance cavity, a microchannel, and a fluid exit orifice, the microchannel having a length in the range of from about 70 μm to about 150 μm.

2. The device of claim 1, wherein the ejector plate has a central open region aligned with the generator plate, and the piezoelectric actuator is coupled to a peripheral region of the ejector plate so as to not obstruct the plurality of openings of the generator plate.

3. The device of claim 2, wherein the plurality of openings of the generator plate are disposed in a center region of the generator plate that is uncovered by the piezoelectric actuator and aligned with the central open region of the ejector plate.

4. The device of claim 3, wherein the generator plate has a reduced size relative to the ejector plate, and the size of the generator plate is determined, at least in part, by the area occupied by the center region and the arrangement of the plurality of openings.

5. The device of claim 1, having an average ejected droplet diameter greater than 15 microns, the stream of droplets having low entrained airflow such that the stream of droplets deposit on a target during use.

6. The device of claim 1, wherein the ejector mechanism is configured to eject a stream of droplets such that at least about 75% of the mass of the ejected droplets deposit on the target.

7. The device of claim 1, wherein the ejector mechanism is configured to eject a stream of droplets having an average ejected droplet diameter in the range of 20 to 400 microns.

8. The device of claim 1, wherein the ejecting mechanism is configured to eject a stream of droplets having an average initial ejected velocity in the range of 0.5 m/s to 20 m/s.

* * * * *